US006596501B2

(12) United States Patent
Roth

(10) Patent No.: US 6,596,501 B2
(45) Date of Patent: Jul. 22, 2003

(54) METHOD OF DIAGNOSING AUTOIMMUNE DISEASE

(75) Inventor: Mark Roth, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 09/256,497

(22) Filed: Feb. 23, 1999

(65) Prior Publication Data

US 2003/0013134 A1 Jan. 16, 2003

Related U.S. Application Data

(60) Provisional application No. 60/075,525, filed on Feb. 23, 1998, and provisional application No. 60/075,904, filed on Feb. 25, 1998.

(51) Int. Cl.$^7$ .................... G01N 33/543; G01N 33/564
(52) U.S. Cl. .................... 435/7.21; 435/7.95; 436/506; 436/508; 436/515; 436/518
(58) Field of Search .............................. 435/7.21, 7.95; 436/506, 508, 515, 518

(56) References Cited

U.S. PATENT DOCUMENTS

| | | | |
|---|---|---|---|
| 3,850,752 A | 11/1974 | Schuurs et al. | |
| 3,939,350 A | 2/1976 | Kronick et al. | 250/365 |
| 3,996,345 A | 12/1976 | Ullman et al. | |
| 3,997,657 A | * 12/1976 | Dziobkowski et al. | 436/506 |
| 4,275,149 A | 6/1981 | Litman et al. | 435/7 |
| 4,277,437 A | 7/1981 | Maggio | 422/61 |
| 4,366,241 A | 12/1982 | Tom et al. | 435/7 |
| 4,367,110 A | 1/1983 | Yoshikawa | 156/219 |
| 4,452,901 A | 6/1984 | Gordon et al. | 436/506 |
| 4,554,101 A | 11/1985 | Hopp | |
| 4,668,621 A | 5/1987 | Doellgast | 435/13 |
| 4,366,241 A | 10/1988 | Tome et al. | |
| 5,071,745 A | 12/1991 | Triscott et al. | 435/7.4 |
| 5,320,940 A | 6/1994 | Talal et al. | 435/5 |

FOREIGN PATENT DOCUMENTS

| | | |
|---|---|---|
| EP | 0273085 | 12/1986 |
| EP | 373908 | 12/1989 |
| WO | WO 98/39658 | 9/1998 |

OTHER PUBLICATIONS

Utz et al, Jour. Exper. Med., 185(5), 843–854, 1997.*
R. M. Nakamura, Immunopathology: Clinical Laboratory Concepts and Methods, Little, Brown and Co., Boston, pp. 247–288, 1974.*
Aebersold et al., "Internal amino acid sequence analysis of proteins separated by one or two–dimensional gel electrophoresis after in situ protease digestion on nitrocellulose," *Proc. Natl. Acad. Sci.,* 84:6970–6974, 1987.
Alarcon–Segovia and Sanchez–Guerrero, "Primary antiphospholipid syndrome," *J. Rheumatol.,* 16:482–488, 1989.
Asherson et al., "The 'primary' antiphospholipid syndrome: Major clinical and serological features," *Medicine* 68(6):366–374, 1989.

Birney et al., "Analysis of the RNA–recognition motif and RS and RGG domains: conservation in metazoan pre–mRNA splicing factors," *Nucleic Acids Res.,* 21(25):5803–5816, 1993.

Cáceres and Krainer, "Functional analysis of pre–mRNA splicing factor SF2/ASF structural domains," *EMBO J.,* 12(12)4715–4726, 1993.

Cohen et al., "Preliminary criteria for the classification of systemic lupus erythematosus," *Bulletin., Rheum. Dis.,* 21(9):643–648, 1971.

Craft and Hardin, "Immunoprecipitation Assays for the detection of soluble nuclear and cytoplasmic nucleoproteins," In: *Manual of Clinical Laboratory Immunology,* (4th Ed.), Rose et al., (eds.), 110:747–754, 1992.

Dignam et al., "Accurate transcription initiation by RNA polymerase II in a soluble extract from isolated mammalian nuclei," *Nucleic Acids Res.,* 11(5):1475–1489, 1983.

Esdaile et al., "Routine immunologic tests in systemic lupus erythematosus: Is there a need for more studies?" *J. Rheumatol.,* 23(11):1891–1896, 1996.

Fritzler, "Immunofluorescent antinuclear antibody test," In: *Manual of Clinical Laboratory Immunology,* (4th Ed.), Rose et al., (eds.). 106:724–729, 1992.

Fu, "The Superfamily of arginine/serine–rich splicing factors" In:*RNA,* 1:663–680, 1995.

Harlow and Lane, "Immunoassays," In: *Antibodies Manual, a Laboratory Manual,* 14:558, 562–569, 1988.

Harris, "Anticardiolipin antibodies and autoimmune dieases" In: *Curr. Op. Rheum.,* 1:215–220, 1989.

Imai et al., "Putative Splicing Factor Autoantigen in Hepatocellular Carcinoma" In: *J. Clin. Invest.,* 93:2419–2426, 1993.

James et al., "An Increased Prevalence of Epstein–Barr virus infection in young patients suggest a possible etiology for systemic Lupus Erythematosus" In: *J. Clin Invest.* 100(12):3019–3026, 1997.

(List continued on next page.)

Primary Examiner—David Saunders

(57) ABSTRACT

The present invention relates to diagnostic applications. For autoimmune diseases more particularly, it is demonstrated herein that individuals with SLE, APLA, MCDS and PSS have antibodies that are specific for SR proteins. Thus, in particular aspects the present invention provides methods and compositions for diagnosing autoimmune disease using SR proteins and antibodies to detect the presence of SR protein-specific antibodies in an individual suspected of having autoimmune disease, wherein the presence of such antibodies is indicative of said individual suffering from autoimmune disease.

16 Claims, 7 Drawing Sheets

OTHER PUBLICATIONS

Khamashta and Hughes, "Antiphospholipid antibodies and antiphospholipid syndrome" In. *Curr. Op. Rheumatol.*, 7:389–394, 1995.

Kim et al., "The Drosophila RNA–binding protein RBP1 is localized to transcriptionally active sites of chromosomes and shows a funtioanl similarity to human splicing factor ASF/SF2", *Genes & Dev.*, 6:2569–2579, 1992.

Kim et al., "Splicing Factors Associate with Hyperphosphorylated RNA polymerase II in the absence of Pre–mRNA," *J. Cell Biol.*, 136(1):19–28, 1997.

Kraus and Lis, "The concentration of B52, an essential splicing factor and regulator of splice site choice in vitro, is critical for Drosophila development," *Mol. Cell. Biol.*, 14(8):5360–5370, 1994.

Lane et al., "Complete amino acid sequence of the FK506 and Rapamycin binding protein, FKBP, isolated from calf thymus," *J. Prot. Chem*, 10:515–160, 1991.

Lockshin, "Antiphospholipid antibody syndrome," *Rheum. Dis. Clin. North Am.*, 20(1):45–58, 2994.

Luo et al., "Effect of dehydroepiandrosterone on bone mass, serum lipids, and dimethylbenz(a)antracene–induced mammary carcinoma in the rate," *Endocrinology*, 138(8):3387–3394, 1997.

Luo et al., "Combined effects of dehydroepiandrosterone and EM–800 on bone mass, serum lipids, and the development of dimethylbenz(A)anthracene–induced mammary carcinoma in the rat," *Endocrinology*, 138(10):4435–4444, 1997.

Neugebauer and Roth, "Distribution of pre–mRNA splicing factors at sites of RNA polymerase II transcription," *Genes Dev.*, 11:1148–1159, 1997.

Neugebauer et al., "A conserved epitope on a subset of SR proteins defines a larger family of pre–mRNA splicing factors," *J. Cell Biol.*, 129:899–908, 1995.

Ou et al., "Screening of SLE sera using purified recombinant Sm–D1 protein from a baculovirus expression system," *Clin. Immunol. Immunopathol.*, 83:310–317, 1997.

Pettersson et al., "The structure of mammalian small nuclear ribonucleoproteins," *J. Biol. Chem.*, 259:5907–5914, 1984.

Picking et al., "Anti–RNA polymerase I antibodies in the urine of patients with systemic lupus erythematosus," *J. Rheumatol.*, 17:1308–1313, 1990.

Pisetsky et al., "Systemic lupus erythematosus," *Advances in Rheumatol.*, 81(1):113–128, 1997.

Query and Keene, "A human autoimmune protein associated with U1 RNA contains a region of homology that is cross-–reactive with retroviral p30$^{gag}$ antigen," *Cell*, 51:211–220, 1987.

Reichlin, "Antibodies to ribonuclear proteins," *Rheumatic Disease Clinics of North America*, 20(1):29–43, 1994.

Ring and Lis, "The SR protein B52/SRp55 is essential for Drosophila development," *Mol. Cell Biol.* 14:7499–7506, 1994.

Rokeach et al., Overproduction of a human snRNP–associated Sm–D autoantigen in *E. coli* and *Saccharomyces cerevisiae*, Gene, 118:247–253, 1992.

Roth et al., "A conserved family of nuclear phosphoproteins localized to sites of polymerase II transcription," *J. Cell Biol.*, 115:587–596, 1991.

Rupp and Weintraub, "Ubiquitous MyoD transcription at the midblastula transition precedes induction–depdndent MyoD expression in presumptive mesoderm of *X. laevis,*" *Cell*, 65:927–937, 1991.

Shapiro, "The lupus anticoagulant/antiphospholipid syndrome," *Annu. Rev. Med.*, 47:533–53, 1996.

Stetler et al., "Anti–RNA polymerase I antibodies in the sera of MRL lupus mice at the initial stages of disease are directed primarily against phosphorylation–dependent epitopes," *Autoimmunity*, 12:29–36, 1992.

Suzuki et al., "Hormones and lupus: defective dehydroepiandrosterone activity induces imparied interleukin–2 activity of T lymphocytes in patients with systemic lupus erythematosus," *Ann. de Medecine Interne*, 147:248–252, 1996.

Tacke and Manley, "The human splicing factors ASF/SF2 and SC35 possess distinct, functionally significant RNA binding specificities," *Embo J.*, 14:3540–3551, 1995.

Tan, "Autoantibodies and autoimmunity: a three–decade prerspective," *Annals NY Acad. Med.*, 815:1–14, 1997.

Tazi et al., "Thiophosphorylation of U1–70K protein inhibits pre–mRNA splicing," *Nature*, 363:283–286, 1993.

Ting and Hsieh, "A long term immunological study of childhood onset systemic lupus erythematosus," *Ann. Rheum. Dis.*, 51:45–51, 1992.

Tomer et al., "Pathogenic significance and diagnostic value of lupus autoantibodies," *Int. Arch. Allergy, Immunol.*, 100:293–306, 1993.

Valcärcel and Green, "The SR protein family: pleiotropic functions in pre–mRNA splicing," *TIBS*, 21:296–301, 1996.

van Vollenhoven et al., "Dehydroepiandrosterone in systemic lupus erythematosus," *Arthritis & Rheumatism*, 38:1826–1831, 1995.

Venables, "Diagnosis and treatment of systemic lupus erythematosus," *British Med. J.*, 307:663–666, 1993.

Wang and Manley, "Overexpression of the SR proteins ASF/SF2 and SC35 influences alternative splicing in vivo in diverse ways," *RNA*, 1:335–346, 1995.

Weiner et al., "Double–blind pilot trial of oral tolerization with myelin antigens in multiple sclerosis,"*Science*, 259:1321, 1993.

Wilson and Sanders, "Immunodiffusion assays for antibodies to small nuclear ribonucleoproteins and other cellular antigens," In: *Manual of Clinical Laboratory Immunology*, (4th Ed.) Rose et al., (eds.), 109:741–746, 1992.

Yitzaki et al., "Phosphorylated Ser/Arg–rich proteins: limiting factors in the assembly of 200S large nuclear ribonucleoprotein particles," *Proc. Natl. Acad. Sci.*, 93:8830–8835, 1996.

Zahler and Roth, "Distinct functions of SR proteins in recruitment of U1 small nuclear ribonucleoprotein to alternative 5' splice sites," *Proc. Natl. Acad. Sci. USA*, 92:2642–2646, 1995.

Zahler et al., "Distinct functions of SR proteins in alternative pre–mRNA splicing," *Science*, 260:219–222, 1993.

Zahler et al., "SR proteins: a conserved family of pre–mRNA splicing factors," *Genes Dev.*, 6:837–847, 1992.

Zonana–Nacach et al., "Measurement of clinical activity of systemic lupus erythematosus and laboratory abnormalities: a 12–month prospective study," *J. Rheumatol.*, 22(1):45–9, 1995.

Zuo and Manley, "Functional domains of the human splicing factor ASF/SF2," *EMBO J.*, 12:4727–4737, 1993.

Utz et al., "Association of phosphorylated serine/arginine (SR) splicing factors with the U1–small ribonucleoprotein (snRNP) autoantigen complex accompanies apoptotic cell death," *J. Exp. Med.*, 187(4):547–560, 1998.

\* cited by examiner

METHOD OF DIAGNOSING AUTOIMMUNE DISEASE

The present application claims the priority of co-pending U.S. Provisional Patent Application Serial No. 60/075,525, filed Feb. 23, 1998, and U.S. Provisional Patent Application Serial No. 60/075,904, filed Feb. 25, 1998, the entire disclosures of which are incorporated herein by reference without disclaimer.

The government may own rights in the present invention pursuant to grant number GM48435-01A2 from the National Institutes of Health

BACKGROUND OF THE INVENTION

1. Field of the Invention

The present invention relates generally to the field of diagnosing autoimmune disease. More particularly, it concerns the use of specific antigens to detect the presence of SR protein-specific antibodies in an individual suspected of having autoimmune disease, wherein the presence of such antibodies is indicative of said individual suffering from autoimmune disease.

2. Description of Related Art

Autoimmune diseases are known to afflict a significant portion of the population. Some of the more common autoimmune diseases include, among others, scleroderma, systemic lupus erythrematosus and mixed connective tissue disease. These diseases are characterized by the presence of a multitude of autoreactive antibodies that arise spontaneously. To date, high levels of circulating autoantibodies to DNA are the best evidence of these maladies.

In the blood of systemic lupus erythematosus (SLE) patients, there typically are found antibodies directed against one or more components of cell nuclei. Certain manifestations of SLE seem to be associated with the presence of different anti-nuclear antibodies and genetic markers, raising the possibility that SLE may be a family of diseases (Mills, 1994). The more common type of lupus erythematosus, discoid lupus erythematosus (DLE), affects exposed areas of the skin. The more serious and fatal form, systemic lupus erythematosus (SLE), affects many systems of the body, including the joints and the kidneys.

SLE is highly variable in its clinical presentation and affects individuals with an intensity that varies over time. Among the organs targeted in this disease are skin, joints kidneys, nervous system serosal surfaces and blood. These manifestations do not appear synchronously over time. Months or years can pass before a definitive diagnosis of a multisystem disease is ascertained.

Regardless of the clinical manifestations of the disease, patients with lupus almost invariably express anti-nuclear antibodies (Mohan, et al., 1993; Mills, 1994; Swaak, et al., 1986, ter Borg, et al., 1990). Such antibodies also are produced in most other rheumatic diseases (Tan at al., 1989), are produced transiently in viral infections and are present, usually in low titers, in about two percent of the normal population. Of the many anti-nuclear antibodies produced, two are considered diagnostic for SLE, namely, anti-double stranded DNA antibodies (anti-dsDNA, Casals, et al., 1964; Tan et al., 1966) and antibodies to Sm (anti-Sm; Reichlin, 1994). Anti-dsDNA antibodies bind sites on the helical backbone of the native DNA. The anti-Sm bind to proteins on an RNA-protein complex termed snRNP (small nuclear ribonucleoprotein complex; Tan, 1989). Further, in addition to these two antibodies, patients with SLE produce a variety of other autoantibodies which, although not disease specific, are characteristic of the disease.

Although anti-dsDNA and anti-Sm are disease-specific, they do not occur in all patients. Thus, despite the presence of such antibodies, a clear diagnostic assay for individuals with SLE is not available due to the heterogeneous nature of SLE and other autoimmune diseases, requiring the diagnosis to be based on an array of different criteria. Indeed, in order to be classified as lupus, an individual must show at least 4 out of 14 criteria selected from such wide ranging characteristics as malar rash, discoid rash, photosensitivity, oral ulceration, arthritis, serositis, renal defects, neurological disorder (seizures, psychoses), hematological disorder (hemolytic anemia, leukopenia, lymphopenia, thrombocytopenia), immunological disorders (positive LE cell preparation, anti-DNA, anti-Sm, false-positive for syphilis) and the presence of anti-nuclear antibody. These characteristics are not exclusive to lupus but may manifest in other connective tissue disease (Tan, 1982). Furthermore, these criteria are limited as definitive manifestations of lupus. For example, those characterized by low serum complement and/or vasiculitis are not characterizable by these criteria because they lack diagnostic specificity.

Autoimmune diseases typically cause a great deal of discomfort and pain in the patient. Clearly, there is a need for a rapid, distinctive and definitive assay that will be diagnostic for SLE and other autoimmune diseases. This rapid diagnosis would aid the clinician in properly prescribing an effective therapeutic regimen to alleviate the pain and symptoms associated with the disease.

SUMMARY OF THE INVENTION

Thus, in order to facilitate a diagnosis, the present invention provides a method of diagnosing an autoimmune disease in a mammal comprising the steps of obtaining an antibody-containing sample; contacting the sample with a composition comprising an SR antigen; and detecting the presence of an SR antigen/anti-SR antibody complex; wherein the presence of an SR antigen/anti-SR antibody complex is diagnostic for an autoimmune disease.

In particularly preferred embodiments, the autoimmune disease is a systemic autoimmune disease. In more particular embodiments, the systemic autoimmune disease may be selected from the group consisting of systemic lupus erythematosus (SLE), progressive systemic scleroderma, mixed connective tissue disease and antiphospholipid syndrome.

In preferred embodiments, the sample tested may be blood, plasma, serum or any other tissue sample employed in the diagnostic assays. In certain embodiments, the determining comprises the use of a technique selected from the group consisting of ELISA, RIA, immunoprecipitation and Western blotting. In those preferred embodiments, in which ELISA is used the ELISA may be a sandwich ELISA.

In preferred embodiments, the sandwich ELISA comprises the steps of providing a preparation comprising an SR antigen bound to a support; contacting the preparation with the sample whereby an SR antigen/anti-SR antibody complex is formed; and contacting the complex with a detection agent.

It is contemplated that the detection agent may be an anti-Fc antibody that binds the anti-SR antibody. In particularly preferred embodiments, the antibody is labeled with a label selected from the group consisting of a radiolabel, an enzyme, biotin, a dye, a fluorescent tag label, a hapten and a luminescent label. In certain embodiments, the fluorescent tag may be selected from the group consisting of fluorescein, rhodamine, luciferase and green fluorescent protein. In other embodiments, the dye may be selected from the group consisting of phycoerythrin, phycocyanin, allophycocyanin, texas red and o-phthaldehyde. The enzyme may be alkaline phosphatase, or horseradish peroxidase. In defined aspects the support may be any solid support that is routinely used in the art, for example a microtiter plate, a polystyrene bead, test tube or dipstick. In particular embodiments, the SR antigen may be bound to the solid support using an anti-SR antibody.

Also contemplated herein is a kit comprising an SR protein preparation, and a suitable container means therefor. The kit may further comprise a first antibody preparation that binds to an anti-SR antibody and a suitable container means therefor. In alternative and equally preferred embodiments, the kit may further comprise a second antibody preparation that binds to an antigenic determinant on an SR antigen, wherein the second antibody composition is immunoreactive against an epitope distinct from the epitope for the anti-SR antibody composition, and a suitable container means therefor. In certain detailed aspects, the second antibody preparation comprises a detectable label. In other aspects, the SR protein preparation is attached to a support. In particular embodiments, the support is a microtiter plate, polystyrene bead, test tube or dipstick. In particularly preferred embodiments, the anti-SR antibody-binding antibody preparation comprises a detectable label. In defined embodiments, the detectable label is a radiolabel, an enzyme, biotin, a dye, a fluorescent tag label, a hapten and a luminescent label. The enzyme may be alkaline phosphatase or horseradish peroxidase. In those embodiments in which the label is an enzyme, the kit may further comprise a substrate for the enzyme. It is contemplated that all the components of the kits may be suitable packaged as described herein below. Specifically, the kit also may comprise a buffer or diluent, and a suitable container means therefor. Other kit components, including reagent reservoirs, instructions and the like are well known to those of skill in the art.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A. Histogram showing the scores ($A_{450}$) of 57 sera from patients with a variety of autoimmune diseases tested on plates coated with purified human SR proteins. Labeled bars below the x-axis indicated the normal pool, the pool of patients with SLE, and the pool of patients with "other" autoimmune disorders (see Table 3). The study was performed blind with serum diluted 1:50 in blocking solution (see materials and methods) and the data sorted according to disease subsequently. The horizontal line indicates the mean +2 standard deviations from a pool of 44 normal sera. This data is a partial representation of that presented in Table 3.

FIG. 4B. Histogram showing the scores ($A_{450}$) of the same 57 patient sera tested on plates coated with purified, bacterially expressed RE-GST. The bar labeled "C" represents a positive control, the mAb16H3 which binds RE-GST.

FIG. 6A. 63 patients with SLE and APLA.

FIG. 6B. 39 patients with SLE but without APLA or a history of clotting.

FIG. 6C. 29 patients without SLE but with APLA and no clotting history.

FIG. 6D. The pool of 44 normal sera.

FIGS. 6A–D are the groups described by the data shown in Table 4 (see examples).

DESCRIPTION OF ILLUSTRATIVE EMBODIMENTS

Figure 1:
FIG. 1. Domain Structure of human SR proteins (taken from Valcarcel and Green, 1996)

Most autoimmune diseases are characterized by the presence and production of autoantibodies, and many such autoantibodies are used as markers for such diseases. However, in the majority of connective tissue disorders, the relationship between the pathogenesis of disease and autoantibody production has not been explicitly resolved. Furthermore, these diseases are generally multisystemic, and their heterogeneous nature makes early and definitive diagnosis a challenge. Even with the availability of disease-specific autoantibodies, a clear diagnosis of these diseases requires that a number of different assays be performed. This is, at best, laborious. The present invention, for the first time, provides a clear correlation between the detection of particular antibodies and the presence of an autoimmune disease.

The SR proteins are a family of proteins with arginine serine-rich domains involved in pre-mRNA splicing (Valcarcel and Green, 1996). The present inventor has found that systemic autoimmune diseases are characterized by the presence of antibodies against SR proteins. Thus, the present invention provides methods of diagnosing autoimmune disease by identifying the presence of an antibody against SR protein antigens. The methods and compositions for such an assay are discussed in detail herein below.

A. Autoimmune Diseases

Autoantibodies are the hallmark of autoimmune disease. Most autoimmune diseases are characterized by the production of autoantibodies, and some of these antibodies can be used as markers of these diseases. However, in most connective tissue disease, the relationship between the autoantibody and the pathogenesis of disease has not been elucidated (Tomer et al., 1993). Thus, it is not known whether the autoantibodies induce tissue damage and disease, or are induced by tissue damage and liberation of autoantigens.

The family of autoimmune diseases is expansive. The term "autoimmune disease" refers to disorders wherein the immune system of a mammal mounts a humoral or cellular immune response to the mammal's own tissue or to antigens that are not intrinsically harmful to the mammal, thereby producing tissue injury in such a mammal. The symptoms and degree of severity vary from patient to patient. Further, the clinical features of the disease in a patient vary dramatically with time.

Examples of autoimmune disorders are numerous and include, but are not limited to, systemic lupus erythematosus, rheumatoid arthritis and type I diabetes. Autoimmune diseases also include acute glomerulonephritis, Addison's disease, adult onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, Crohn's disease, dermatomyositis, dilated cardiomyopathy, eosinophilia-myalgia syndrome, epidermolisis bullosa acquisita (EBA), giant cell arteritis, Goodpasture's syndrome, Graves' disease, Guillain-Barre syndrome, hemochromatosis, Henoch-Schonlein purpura, idiopathic IgA nephropathy, insulin-dependent diabetes mellitus (IDDM), juvenile rheumatoid arthritis, Lambert-Eaton syndrome, linear IgA dermatosis, lupus erythematosus, multiple sclerosis, myasthenia gravis, myocarditis, narcolepsy, necrotizing vasculitis, neonatal lupus syndrome (NLE), nephrotic syndrome, pemphigoid, phemphigus, polymyositis, primary sclerosing cholangitis, psoriasis, rapidly progressive glomerulonephritis (RPGN), Reiter's syndrome, rheumatoid arthritis, scleroderma, Sjogren's syndrome, stiff-man syndrome, thyroiditis, and ulcerative colitis. This is not intended to be an exhaustive list but rather, it is intended to demonstrate that autoimmunity is a wide ranging clinical phenomenom. Exemplary diseases in this field such as systemic lupus erythematosus, rheumatoid arthritis, mixed connective tissue disease and APLS are discussed in further detail herein below, with a view to providing some understanding of the problems involved in clinical diagnoses and treatment of these debilitating and potentially fatal disorders.

a. Systemic Lupus Erythematosus (SLE)

SLE is a febrile, inflammatory, multisystem disease that is best characterized by a number of features. Clinically, it is an unpredictable, remitting and relapsing disease of acute and insidious onset. It may involve any organ in the body, but it principally affects the skin, kidneys, serosal membranes, joints and the heart. Anatomically, all the sites involved in the disease have vascular lesions comprising fibrinoid deposits. Immunologically, the disease involves a bewildering array of autoantibodies and especially anti-nuclear antibodies.

The clinical manifestations of SLE are so varied that it bears a great deal of similarity to a plethora of other autoimmune diseases including rheumatoid arthritis and polymyositis, amongst others. This heterogeneity has necessitated the use of a list of diagnostic criteria to be fulfilled before a definitive diagnosis of the disease can be attained. There are at least 14 criteria that can be examined; if four or more of these criteria are present, then SLE is indicated (Cohen, et al., 1971). These criteria include, facial erythema, discoid lupus rash, Raynaud's phenomenom, alopecia, photosensitivity, oral nasal or pharyngeal ulceration, arthritis without deformity, LE cells, false positive tests for syphilis, proteinurea (>3.5 g/day), pleuritis, pericarditis, psychosis, convulsions hemolytic anemia, leukopenia and thrombocytopenia.

Pathogenesis of the disease is of an autoimmune type, thought to involve anti-nuclear antibodies (ANAs) amongst others. ANAs are targeted against soluble and particulate nucleoproteins of both double-stranded and single-stranded DNA, single-stranded and double-stranded RNA as well as a saline extractable nuclear constituent (Sm antigen). Additionally, antibodies have been identified against the mitochondria, ribosomes, lysosomes, a soluble cytoplasmic fraction, red cells, white cells, platelets and blood clotting factors (Weidermann and Meischer, 1965). Given the presence of all these autoantibodies, remarkably little is known about the mechanisms of their emergence and the diagnosis and treatment of this disease is still dependent on numerous factors.

Often, SLE patients also develop antiphospholipid antibodies (APLS) (described below) and this is associated with increased arterial and venous thrombosis, thrombocytopenia, neurologic disorders, and recurrent fetal loss.

There is no specific treatment for SLE, but several drugs are known to modify the disease so that the symptoms are tolerable (Lieberman et al., 1988; Steinberg and Steinberg, 1991; Vyse and Walport, 1993; Wilke et al., 1991, Miller, 1992; Lubbe et al., 1983; Silman et al., 1988). These treatment regimens include non-steroidal anti-inflammatory drugs (NSAIDs; Kimberly, 1988) and analgesic; steroids, such as, prednisolone (Lubbe et al., 1983) and methylprednisolone (Edwards et al., 1987), hydroxychloroquine, azathioprine (Silman et al., 1988) and cyclophosphamide (Steinberg and Steinberg, 1991). The potential benefit of each of these treatments is counterbalanced by side effects, which are almost always inevitable. Thus, precautions are a must, and these include mandatory full blood counts to monitor marrow depression, giving mesna as a protective against cystitis and bladder carcinoma. One of the most common causes of death in SLE patients is secondary infection (Gladman, 1992). Although the causes of SLE are unknown, certain factors definitely exacerbate the symptoms of the disease, these include UV light and certain hormones. Such factors can be avoided using barrier creams and avoiding contraceptives containing estrogens.

It has been conceded by those of skill in the art (Venables, 1993) that little has changed in the diagnosis of SLE in the past two decades. The present invention, for the first time, provides a definitive diagnostic test for SLE that will be of great use in facilitating a better management of the disease.

b. Systemic Sclerosis

Progressive systemic sclerosis also is known as scleroderma. It is characterized by inflammatory and fibrotic changes throughout the interstitium of may organs of the body. Although skin involvement is the primary site of presenting the symptoms, it is the visceral involvement of the gastrointestinal tract, lungs, kidneys heart and striated muscles that produces the major disability and life-threatening features of this disorder.

PSS is a disease of unknown etiology. It has many of the features described for RA and SLE; however, it is distinctive in its cutaneous changes. Most patients first develop Reynaud's phenomenon, which may be present for many years before the appearance of skin changes. Progressive deposition of collagen in the skin leads to atrophy of the hands with an accompanying stiffness and eventually total immobilization of the joints. General disability results when the trunk and extremities are affected. The course of the disease is difficult to predict. In most patients, the disease proceeds in a gradual deleterious path over the span of many years. The present invention provides a diagnostic for this disease in that patients having PSS have been shown to have antibodies against SR proteins.

c. Polymyositis (Dermatomyositis)

Another exemplary autoimmune disease that can be diagnosed according to the present invention is polymyositis, which also is known as dermatomyositis when it present a skin rash. It is a chronic inflammatory myopathy of uncertain cause. Clinically, it is characterized by symmetric muscle weakness and varying degrees of pain, swelling and atrophy of affected muscles, often accompanies by a rash about the eyes. Anatomically, the dominant features are focal areas of muscle inflammation leading to individual muscle cell atrophy, loss or hypertrophy.

In the clinical course of polymyositis, the principal clinical finding is symmetric muscular weakness sometimes insidious but occasionally acute in onset. Acute cases often are febrile. The diagnosis of polymyositis cannot be entertained in the absence of muscular involvement.

d. Mixed Connective Tissue Disease

Mixed connective tissue disease (MCTD) is considered a rheumatic disease syndrome characterized by overlapping clinical features similar to those of SLE, progressive systemic sclerosis and polymyositis/dermatomyositis. This disease is characterized and differentiated from SLE, PSS and polymyositis/dermatomyositis by the presence of very high titers of circulating anti-RNP antigen antibodies. While the clinical features of this disease suggest several connective tissue diseases, the presence of high titers of anti-RNP antibodies and the relative absence of other anti-nuclear antibodies, the normal clearance of immune complexes via the reticuloendothelial system, abnormalities of immunoregulatory T cell circuits, frequent pulmonary hypertension and associated proliferative vasculopathy with minimal fibrosis distinguish MCTD from other systemic autoimmune diseases. About 80% of MCTD patients are female, with an age range from 5 to 80 years with a mean of 37 years. The overall mortality has been reported to be about 13%, with a mean disease duration varying from six to twelve years. Recently, silicone breast implants have been associated with a group of symptoms similar to those observed in connective tissue disorders, rheumatoid arthritis, SLE or polymyocytis such as Raynaud's phenomenon, skin rash and hair loss (Ellis et al., 1997; Teuber et al., 1995a; Teuber et al., 1995b; Scharp et al., 1972). Increasingly, it is becoming recognized that breast implant components may induce immunotoxic or inflammatory effects.

Patients typically present first with Raynaud's phenomenon, sometimes many years preceding the other clinical manifestations. Patients exhibit polyarthralgia or arthritis, swollen hands, inflammatory proximal myopathy, esophageal hypomotility and pulmonary disease. Some patients exhibit a fever of unknown origin. Frequently, initial clinical manifestations suggest SLE, PSS, polymyositis/dermatomyositis or RA. The most frequent skin manifestation is swelling of the hands. Other skin manifestations include lupus-like rashes, erythematous patches over the knuckles, diffuse nonscarring alopecia. The disease tends to proceed from a more limited disease to more widespread involvement with transitions in clinical pattern over time.

Treatment of these patients is generally similar to treatment of SLE. Patients are treated with corticosteroids, particularly if treatment is in the early stage of the disease. Mild disease is treated with salicylates, other non-steroidal anti-inflammatory drugs, anti malarial s or very low doses of corticosteroids. In progressive and widespread disease, treatment often relies on high dose corticosteroids sometimes combined with cytotoxic drugs.

Almost all MCTD patients demonstrate high titers of anti-RNP antibodies. Immunofluorescent staining of tissue sections reveals a speckled staining pattern. Diagnosis of MCTD is generally considered when patients present with overlapping clinical features. These features in combination with the detection of high titers of anti-RNP antibodies permit a presumptive diagnosis of MCTD. The present invention provides a diagnostic test for MCTD. As shown in more detail herein, MCTD-diagnosed patients exhibited high titers of anti-SR antibodies.

e. Antiphospholipid Syndrome

Antiphospholipid syndrome has the hallmark presence of lupus anticoagulant (LAC) or anticardiolipin antibody (ACA) activity. (Shapiro, 1996). The antiphospholipid syndrome is defined as a clinical disorder with recurrent arterial and venous thrombotic events, pregnancy wastage and/or thrombocytopenia in the presence of the lupus anticoagulant and/or moderate to high positive anticardiolipin test. Both a primary form, in patients without clinically or serologically evident autoimmune disorders, and a secondary form, usually in patients with systemic lupus erythematosus, are recognized.

The presence of antiphospholipid antibodies mainly has been demonstrated in patients with systemic lupus erythematosus with the prevalence ranging between 20% and 50%. Patients with SLE manifest what is described as secondary APLS, this results in heightened neurological disorders and arterial events. The exact mechanism by which antiphospholipid antibodies cause clinical manifestations of the syndrome is unclear. Strokes, often preceded by transient ischemia attacks, are the most frequent arterial events encountered. The cutaneous manifestations associated with the antiphospholipid syndrome are multiple. Skin ulceration and cutaneous necrosis and infarction are often seen.

Thrombosis may be present in small, medium, or large venous or arterial sites. The presentation is episodic and unpredictable. Venous thrombosis of a leg or arm, renal vein thrombosis, the Budd-Chiari syndrome, pulmonary embolism, Addison's disease, retinal, sagital, pelvic, mesenteric, portal and axillary vein thrombosis have all been described. When an arterial site is involved, the manifestations may vary between the clinical features of a stroke or transient ischemic attack. When other arterial vascular beds are affected, such as the retinal, coronary, brachial, mesenteric, renal (interlobular arteries, arterioles and glomerular capillaries) and dermal arterioles, the clinical presentations are directly related to involved site.

Some patients may present with recurrent pregnancy losses often, but not always, in late second or third trimester of gestation. Nervous system disorders also are a consequence of APLS. Most neurologic abnormalities are consequent to cerebrovascular thrombosis, which result in reversible or fixed focal deficit. The neurological manifestations of the patient with APLS are much wider transient ischemic attacks, cerebral infarcts and cerebral venous thrombosis. Other neuralgic presentations include epilepsy, transverse myelopathy, Guillain-Barré syndrome and chorea. APLS also is associated with renal vein thrombosis, Addison's disease, gut ischemia, Budd-Chiari syndrome, thrombocytopenia, autoimmune hemolytic anemia, idiopathic thrombocytopenic purpura, cardiac valve abnormalities (insufficiency mitral and aortic) and Libman-Sacks endocarditis. Further, dermatologic manifestations are extremely frequent, including livedo reticularis, leg ulceration, distal cutaneous ischemia or necrosis, superficial thrombophlebitis, blue-toe syndrome, splinter hemorrhage and porcelain-white scars are also seen.

Laboratory diagnosis is based on the presence of LAC antibodies and ACA antibodies. The lupus anticoagulant is an immunoglobulin that prolongs clotting time in vitro because phospholipids present in the plasma agglutinate, thereby preventing their participation as cofactors in coagulation steps. Its in vitro action appears to be the inhibition of the conversion of prothrombin to thrombin.

Since phospholipids are not very antigenic, the true antigen for the lupus anticoagulant antibody probably includes a plasma protein. The heterogeneity of the lupus anticoagulant can, therefore, be explained by the concept that the lupus anticoagulants are a family of antiphospholipid-plasma antibodies, with subgroups defined by both the phospholipids and plasma protein involved. Accordingly, no lupus anticoagulant test is 100% sensitive. Therefore, the following criteria are required for a positive lupus anticoagulant test: 1-prolonged partial thromboplastin time, Russel Viper Venom time, or Kaolin clotting time; 2-failure to correct the test by mixing patient plasma with normal plasma (suggesting a clotting inhibitor is present); 3-normalization of the test with freeze-thawed platelets, or phospholipids.

Realizing that cardiolipin was the major antigenic component of the false-positive test for syphilis, a radioimmunoassay was created directed against this phospholipid. Over time, an enzyme-linked assay (ELISA) replaced the radioimmunoassay. Cardiolipin, which is found in the mitocondria, is unlikely to be the antigen against which the antibody reacts in vivo. Nevertheless, because antiphospholipid antibodies cross-react with other negatively charged phospholipids, cardiolipin can serve as a representative antigen in the system.

Anticardiolipin antibody is one of the few autoantibodies for which assays allow the identification and quantification of specific isotypes (IgG, IgM and IgA). The IgG isotype was the major predictor of thrombosis and pregnancy loss while the IgM class was associated especially with hemolytic anemia in addition to thrombosis. Besides the identification of different isotypes, antibody titer seems an useful predictor of pathogenicity (even though it is still not clear that quantity of antibody is the best or the only one). The higher-titer of IgG anticardiolipin antibody (>40GPL) correlates strongly with thrombosis and fetal loss. Most patients with antiphospholipid syndrome have medium to high IgG anticardiolipin antibody levels with or without other isotypes.

Disease management occurs by a treatment of the symptoms of the disease. Acute management of arterial or venous thrombosis in patient with antiphospholipid syndrome is no different from the treatment of other patients with similar complications. Thus, the patient should receive heparin (1000 units/h). Prophylactic oral anticoagulant is advised following venous thrombosis for a prolonged period of time since patients with antiphospholipid syndrome are prone to recurrent thrombosis. In patients with stroke or other arterial thrombotic event, aspirin (80–100 mg/day), aspirin plus dipyridamole, or oral anticoagulation have been used by various groups. When venous thrombosis occurs, an INR>3.5 should be achieved with warfarin. In cases in which thrombosis continues despite adequate anticoagulation, high doses of corticosteroids, initially, and cyclophosphamide have been used in addition to anticoagulation.

Both lupus anticoagulant and anticardiolipin antibody are associated with each of the clinical manifestations of the antiphospholipid syndrome. There is much controversy between the relation of ACA and LAC; thus the test may be positive for one, negative for other, or positive for all. The present invention provides a diagnostic test for APLS, in that patients previously diagnosed with APLS tested positive for antibodies against SR proteins.

As is evident from the discussions presented above, autoimmune diseases manifest themselves in a variety of clinical disorders. There appears to be few or no unifying characteristics that could definitively designate a particular disorder as an autoimmune disorder. The present invention provides a simple diagnostic test that can be used in any number of suspected autoimmune diseases in order to provide a primary diagnosis of autoimmune disease or to confirm the presence of autoimmune disease when used in combination with any one of a number of other diagnostic criteria for the diseases listed above.

B. SR proteins

Most eukaryotic mRNAs are synthesized as precursors that contain intervening intron sequences. The introns are removed in the nucleus, and the flanking exons are spliced together to generate a functional mRNA. Often, the use of alternate splice sites in the same pre-RNA is regulated in a cell-type specific manner, thereby allowing the synthesis of different polypeptides from the same gene.

In 1990, Ge and Manley showed that a single, purified polypeptide, called ASF, when added to standard in vitro splicing reactions, could change the relative use of two competing 5' splice sites of an SV40 early pre-RNA. The sequence of ASF is the same as that of another protein termed SF, required to reconstitute pre-mRNA splicing (Krainer et al., 1991). ASF/SF2 is a splicing factor that can switch between alternative splice-sites when presented in excess, thus implying that physiological variation in the concentration of splicing factors regulates alternative splicing.

ASF/SF2 contains an amino-terminal RNA-binding domain composed of ribonucleoprotein (RNP). The RNP-CS motifs are 70 to 90 amino acids in length. RNP-CS are commonly found in polypeptides that recognize RNA in a sequence specific manner and which have a variety of functions in RNA metabolism. ASF/SF2 also contains a carboxy-terminal region that is rich in arginine-serine dipeptides. Similar modular organization and activities also have been found in SC35, a polypeptide identified as a component of splicing complexes (Fu and Maniatis, 1992)

At about the same time, it was discovered that ASF/SF2 (Genbank sequence HUMSF2P33, incorporated herein by reference) and SC35 (Genbank sequence HUMSC35, incorporated herein by reference) belong to a set of six proteins that can be identified by a monoclonal antibody that recognizes components of transcriptionally active sites both in Xenopus lampbrush and in Drosophila polytene chromosomes (Roth et al., 1991). This group of proteins also includes; a 20 kDa polypeptide (Genbank sequence HUMSRP20, incorporated herein by reference); a 40 kDa polypeptide (Genbank sequence HSU30826, incorporated herein by reference); a 55 kDa polypeptide (Genbank sequence HSU30828, incorporated herein by reference) and a 75 kDa polypeptide (Genbank sequence HUMSRP75, incorporated herein by reference; Zahler et al., 1992). All six proteins were co-purified from various sources by a simple, two-step salt precipitation procedure and were collectively named SR proteins.

SR proteins share a similar domain organization (FIG. 1) and the ability to modulate 5' splice-site choice. In addition, SR proteins can complement cytoplasmic S100 extracts, which lack all six polypeptides, and therefore cannot support splicing reactions. SR proteins belong to a larger family of polypeptides with alternating arginine domains which include snRNP-associated (e.g., U1 70K) and non-snRNP associated (e.g. U2AF) splicing factors, splicing regulators and an increasing number of previously unidentified spliceosomal components (Neugebauer et al., 1995; Fu, 1995). The term SR proteins, however, usually is reserved for the six polypeptides mentioned above and illustrated in FIG. 1, with a few more recent additions that share most of their characteristic features.

The structural and functional similarities among SR proteins suggests that they could perform redundant roles. Depletion or mutation of one particular SR member in Drosophila, however, prevents normal development.(Ring and Lis, 1994; Peng and Mount, 1995), indicating distinct functions in vivo. Although SR proteins are conserved across metazoa and have a ubiquitous tissue distribution, cell-type differences in their relative abundance and activity have been observed (Ring and Lis, 1994; Zahler et al., 1993; Screaton et al., 1995; Zahler et al., 1992; Kim et al., 1992; Zahler and Roth, 1995), suggesting that each cell type might have a distinct pattern of relative SR protein concentrations, which might define alternative splicing decisions. Consistent with this hypothesis, overproduction of a particular SR member in Drosophila causes multiple developmental abnormalities, which could result from aberrant pre-mRNA splicing regulation (Kraus and Lis, 1994).

a. Functions of the Structural Domains

SR proteins have a modular structure consisting of an RNA-binding domain and an arginine-serine-rich (RS) region (FIG. 1). The amino-terminal RNA-binding domain is essential for all the known activities of SR proteins, both in vitro and in vivo (Wang and Manley, 1995; Caceres and Krainer, 1993; Zuo and Manley, 1993). This region consists of one or two repeats of the aforementioned RNP-CS motif. In those SR proteins containing two repeats, the amino acid sequence of the carboxy-terminal motif is less well conserved. This 'degenerate' RNP-CS, however, also contributes to define the overall RNA-binding affinity and specificity of the protein (Cáceres and Krainer, 1993; Tacke and Manley, 1995).

RNA binding. Using iterative selection from a pool or random RNA sequences, different purine-rich-binding consensus sequences have been obtained for ASF/SF2 and SC35 (Tacke and Manley, 1995). The ASF/SF2 consensus is found in some 5' splice-sites and in particular types of exonic sequence, known as the purine-rich exon enhancers, which stimulate the use of weak splice-sites. In fact, ASF/SF2 has been shown independently to bind to both of these sequences (Zuo and Manley, 1994; Sun et al., 1993; Lavigueur et al., 1993). The SC35 consensus also resembles 5' splice-sites (Tacke and Manley, 1995). Little is known about RNA sequences recognized by other SR proteins, and information is urgently needed to understand their functions.

Protein-protein interactions. Arginine-serine (RS) regions are essential for some, but not all functions of SR proteins (Caceres and Krainer, 1993; Zuo and Manley, 1993). These domains differ among SR proteins in their length, number of arginine-serine dipeptides and content of other amino acids (Birney et al., 1993). Presently, it is not clear to what extent these domains are interchangeable. A variety of in vitro and in vivo techniques, including far-western blots, co-precipitation and yeast two-hybrid assays, have revealed that some RS regions can mediate protein-protein interactions (Wu and Maniatis, 1993; Kohtz et al., 1994). Partners for these interactions include other SR proteins; other RS-containing splicing factors and RS-containing splicing regulators. RS domains also are thought to influence RNA binding to promote RNA-RNA annealing or contain sequences that act as subcellular localization domains.

The modular organization of SR proteins suggests a basic mechanism of function. The RNA binding domain could recognize specific splicing signals and recruit other splicing factors by protein-protein or RNA-protein interaction or by RNA-RNA base pairing. This model is similar to that of the action of transcriptional activators in the transcriptional pre initiation complex.

b. Role of Phosphorylation

The monoclonal antibody that allowed the initial purification of the SR protein family recognizes a phosphoepitope in the RS region (Roth et al., 1991), indicating that SR proteins are phosphorylated in vivo. Although a number of kinases have been identified that phosphorylate SR proteins in vitro, the functions of these kinases in vivo still are unclear. (Woppmann et al., 1993; Gui et al., 1994; Colwill et al., 1996; Rossi et al., 1996).

Recent studies have found that cycles of protein phosphorylation-dephosphorylation occur during pre-mRNA splicing. Protein phosphatase inhibitors have been found to prevent catalytic activation of assembled spliceosomes (Hoffman and Grabowski, 1992), whereas an excess of protein phosphatases inhibits spliceosome assembly SR proteins are strong target candidates to mediate these effects (Mermoud, et al., 1994). In this model, their phosphorylation would be required for spliceosome assembly, while their dephosphorylation would be necessary for the spliceosome to undergo catalysis. Phosphorylation of other RS-containing polypeptides, however, also can underlie these effects, as has been shown for the U1 70K protein (Tazi et al., 1993).

c. Role of Autoimmune Antigen in Autoimmunity

Figure 2:
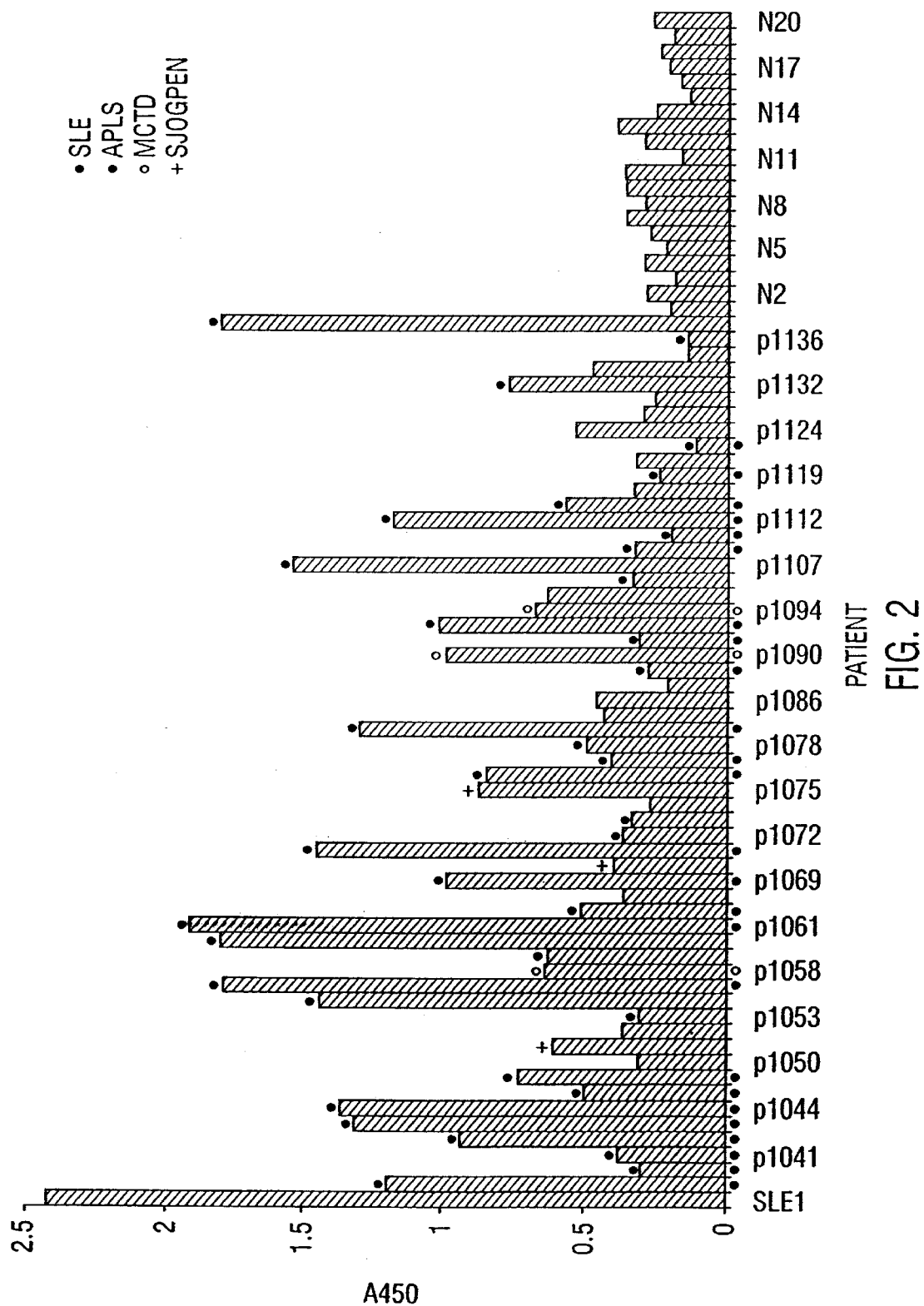
FIG. 2. The presence of autoantisera against SR proteins at a 1:50 dilution in sera from patients with SLE, APLS and MCTD.

The present invention describes a role for SR proteins as autoimmunity antigens. The present invention shows that in patients with SLE, scleroderma, APLS and other auotimmune diseases are characterized by the presence of antibodies against SR proteins (FIG. 2).

In mammals, immunologic tolerance, or the determination of self, commences during the neonatal period when the immune system is still maturing and immature "virgin" lymphocytes are abundant. Tolerance occurs when antigens, such as self antigens, are presented to immature lymphocytes and the lymphocytes are not responsive to these self-antigens. Self-antigens include cell substituents from broken cells such as nucleic acids, proteins, peptides and other degradation products. Thus, a constant supply of self-antigens must be present to induce tolerance in newly arising lymphocytes. The degradation of cell substituents from broken cells is accompanied by removal of post-transcriptional and/or post-translational modifications from the cell substituents. These modifications include acetylation, phosphorylation, poly-ADP ribosylation, ubiquitination and methylation. The demodified antigens are among the self cell substituents that are presented to immature lymphocytes to induce tolerance. For example, degradation of cell substituents may be accompanied by dephosphorylation of phosphorylated substituents by phosphatases. These phosphorylated are among the self cell substituents that are presented to immature lymphocytes to induce tolerance. Autoimmunity reflects the loss of immunologic tolerance. The present inventor suggests that one mechanism for the apparent loss of immunologic tolerance is the inability of the host to efficiently demodify dephosphorylated cellular breakdown products. Thus, within one example the phosphorylated cell substituents are presented and are not recognized as self and thus institute the reactive cascade of the immune response. These include, but are not limited to ss-DNA, ds-DNA, U1 RNP, tRNA, lupus anticoagulant and as demonstrated herein, SR proteins. This new paradigm for the cause of autoimmunity opens new avenues for therapy for patients with autoimmune disease and other diseases associated with the presence of autoantibodies.

The present inventor has demonstrated that in controlled studies using indirect immunofluorescence assays for antinuclear antibodies, patients' sera (diagnosed with systemic lupus erythematosus) were not capable of binding to phosphorylase-treated tissue sections. Briefly, tissue sections were prepared and fixed. Each serum sample was subjected to indirect immunofluorescence on: (1) a phosphatase-pre-treated tissue section to permit dephosphorylation of the tissue section followed by phosphatase inhibitor treatment (β-glycerol phosphatase, in molar excess) and (2) a tissue section that was pre-treated with a phosphatase inhibitor (β-glycerol phosphatase, in molar excess) followed by phosphatase treatment. Results from these studies showed that of the patients shown to be ANA positive, half were negative on tissue sections pre-treated with phosphatase. These patients produced antibodies that are phosphate-sensitive. It follows that patients exhibiting phosphate-sensitive antibodies might benefit from therapies that increase the levels of phosphatases. Dihydroepiandosterone (DHEA), for example, which has been studied as a possible therapeutic agent for the treatment of mild to moderate SLE due to the implication that sex steroid hormones play a role in the pathogenesis of SLE (van Vollenhoven et al., 1995; Suzuki et al., 1996) has been shown to increase serum total alkaline phosphatase levels (Luo et al., 1997 and Luo et al., 1997).

Another factor that adds credence to this hypothesis is that inhibition of phosphatases in a clinical setting results in autoimmune disease. For example, bone marrow transplantation (BMT) often is accompanied with GVHD. In order to ameliorate GVHD, patients undergoing BMT are treated with cyclosporin. Cyclosporin, which is a known inhibitor of phosphatase activity, suppresses the immune response associated with GVHD, but its use results in the autoimmune disease.

C. SR Protein Production

For the purposes of the present invention the SR protein or peptide used as an antigen may be a naturally-occurring SR protein that has been extracted using protein extraction techniques well known to those of skill in the art.

In alternative embodiments, the SR protein peptide or antigen may be a synthetic peptide. In still other embodiments, the peptide may be a recombinant peptide produced through molecular engineering techniques. Particularly preferred will be peptides having alternating phosphoamino acid/basic amino acid motifs. In preferred embodiments, these motifs will comprises alternating phosphorylated acidic amino acid/basic amino acid residues. Even more preferable will be antigenic peptides that mimic SR proteins by having a phospho-serine-arginine dipeptide or a phosphoserine-lysine dipeptide. The present section describes the methods and compositions involved in producing a composition of SR proteins for use as antigens in the present invention. Such antigens are used to either detect the autoimmune disease or in other embodiments, may even be employed in compositions to tolerize individuals against autoimmune disease.

a. SR Polypeptides

SR protein encoding genes or their corresponding cDNA can be inserted into an appropriate cloning vehicle for the production of SR proteins as antigens for the present invention. In addition, sequence variants of the polypeptide can be prepared. These may, for instance, be minor sequence variants of the polypeptide that arise due to natural variation within the population or they may be homologues found in other species. They also may be sequences that do not occur naturally, but that are sufficiently similar that they function similarly and/or elicit an immune response that cross-reacts with natural forms of the polypeptide. Sequence variants can be prepared by standard methods of site-directed mutagenesis such as those described below in the following section.

Another synthetic or recombinant variation of an SR-antigen is a polyepitopic moiety comprising repeats of epitopic determinants found naturally on SR proteins. Such synthetic polyepitopic proteins can be made up of several homomeric repeats of any one SR-protein epitope; or can comprise of two or more heteromeric epitopes expressed on one or several SR protein epitopes. This large polyvalent antigen could be used as a powerful tool for immunodetection of antibodies in the sera, plasma or blood samples obtained from patients. This type of antigen would allow for the formation of a large antigen-antibody complex which can be easily precipitated and detected visibly (see later section on Precipitin Reactions).

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also can include hybrid proteins containing sequences from other proteins and polypeptides which are homologues of the polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptide. These typically are smaller insertions than the fusion proteins described above and are introduced, for example, into a protease cleavage site.

In one embodiment, major antigenic determinants of the polypeptide are identified by an empirical approach in which portions of the gene encoding the polypeptide are expressed in a recombinant host, and the resulting proteins tested for their ability to elicit an immune response. For example, PCR can be used to prepare a range of cDNAs encoding peptides lacking successively longer fragments of the C-terminus of the protein. Alternatively, progressively longer dipeptide sequences comprising alternating phosphoamino acid/basic amino acid motifs can be prepared. In preferred embodiments, these motifs may comprise alternating phosphorylated acidic amino acid/basic amino acid residues. Even more preferable will be antigenic peptides that mimic SR proteins by having a phospho-serine-arginine dipeptide or a phosphoserine-lysine dipeptide. The immunogenic activity of each of these peptides then identifies those fragments or domains of the polypeptide that are essential for this activity. Further experiments in which only a small number of amino acids are removed or added at each iteration then allows the location of other antigenic determinants of the polypeptide.

Another embodiment for the preparation of the polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY,* Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Likely β-turn structure within a polypeptide can be predicted by computer-based algorithms as discussed above. Once the component amino acids of the turn are determined, peptide mimetics can be constructed to achieve a similar spatial orientation of the essential elements of the amino acid side chains.

Modifications and changes may be made in the structure of a gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by change the codons of the DNA sequence, according to the following data.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventor that various changes may be made in the DNA sequences of genes without appreciable loss of their biological utility or activity. Table 1 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982).

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

b. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 nucleotides on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

c. Synthetic Polypeptides

The present invention also describes SR proteins and related peptides for use in various embodiments of the present invention. Because of their relatively small size, the peptides of the invention also can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

d. Genetic Constructs and Their Delivery to Cells

Within certain embodiments, expression vectors can be employed to express various SR genes to produce large amounts of the SR polypeptide product, which then can be purified and used as an antigen in the present invention, or to vaccinate animals to generate antisera or monoclonal antibodies. This section provides a description of the production of genetic constructs and their delivery into cells for such large scale protein expression.

i. Genetic Constructs

Within certain embodiments expression vectors can be employed to express various genes to produce large amounts of the SR polypeptide product, which can then be purified and used as an antigen in the present invention or to vaccinate animals to generate antisera or monoclonal antibodies with which further studies may be conducted. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the SR products are also provided, as is an element that links expression of the drug selection markers to expression of the polypeptide.

Regulatory Elements. Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter refers to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the cell. Thus, where a human cell is used, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Table 2 lists several inducible elements/promoters which may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct. Enhancer/promoter elements contemplated for use with the present invention include but are not limited to Immunoglobulin Heavy Chain, Immunoglobulin Light, Chain T-Cell Receptor, HLA DQ α and DQ β, β-Interferon, Interleukin-2, Interleukin-2 Receptor, MHC Class II 5, MHC Class II HLA-DRα, β-Actin, Muscle Creatine Kinase, Prealbumin (Transthyretin), Elastase I, Metallothionein, Collagenase, Albumin Gene, α-Fetoprotein, τ-Globin, β-Globin, e-fos, c-HA-ras, Insulin, Neural Cell Adhesion Molecule (NCAM), α1-Antitrypsin, H2B (TH2B) Histone, Mouse or Type I Collagen, Glucose-Regulated Proteins (GRP94 and GRP78), Rat Growth Hormone, Human Serum Amyloid A (SAA), Troponin I (TN I), Platelet-Derived Growth Factor, Duchenne Muscular Dystrophy, SV40, Polyoma, Retroviruses, Papilloma Virus, Hepatitis B Virus, Human Immunodeficiency Virus, Cytomegalovirus, Gibbon Ape Leukemia Virus. Inducible promoter elements and their associated inducers are listed in Table 2 below.

TABLE 2

| Element | Inducer |
| --- | --- |
| MT II | Phorbol Ester (TPA), Heavy metals |
| MMTV (mouse mammary tumor virus) | Glucocorticoids |
| β-Interferon | poly(rI)X, poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). Adeno-associated viruses are also useful in this context (Ridgeway, 1988; Baichwal and Sugden, 1986; Hermonat and Muzycska, 1984). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

Selectable Markers. In certain embodiments of the invention, the cells contain nucleic acid constructs for the production of SR antigens, such a cell may be identified by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

Multigene constructs and IRES. In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

ii. Delivery of Genetic Constructs

In order to express the proteins from the expression constructs, the nucleic acids need to be delivered into a cell. There are a number of ways in which nucleic acids may introduced into cells. Several methods, including viral and non-viral transduction methods, are outlined below.

Adenovirus. One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Generation and propagation of adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra Kb of DNA. Combined with the approximately 5.5 Kb of DNA that is replaceable in the E1 and E3 regions, the maximum capacity of the current adenovirus vector is under 7.5 Kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

The nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

The typical adenoviral vector is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the SR gene of interest may also be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992).

Retroviruses. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Adeno-Associated Virus (AAV). AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

The terminal repeats of the AAV vector can be obtained by restriction endonuclease digestion of AAV or a plasmid such as p201, which contains a modified AAV genome (Samulski et al. 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

Other Viral Vectors as Expression Constructs. Other viral vectors may be employed as expression constructs in the present invention. Vectors derived from viruses such as vaccinia virus (Ridgeway, 1988; Baichwal and Sugden, 1986; Coupar et al., 1988) and herpes viruses may be employed. They offer several attractive features for various mammalian cells (Friedmann, 1989; Ridgeway, 1988; Baichwal and Sugden, 1986; Coupar et al., 1988; Horwich et al., 1990).

In vitro studies of hepatitis B viruses showed the virus retained the ability for helper-dependent packaging and reverse transcription despite the deletion of up to 80% of its genome (Horwich et al., 1990), suggesting that large portions of the genome could be replaced with foreign genetic material. The hepatotropism and persistence (integration) are particularly attractive properties for liver-directed gene transfer. Chang et al., 1991, recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Non-viral vectors. Several non-viral methods for the transfer of expression constructs into cultured mammalian cells are contemplated by the present invention. These include calcium phosphate precipitation (Graham and Van Der Eb, 1973; Chen and Okayama, 1987) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al., (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring naked DNA expression constructs into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

e. Cell Culture

In order to produce large quantities of an SR protein from a cell transfected with an expression construct as described herein above, it may be necessary to grow the cell in culture for a period of time to allow protein production to occur. Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

As would be evident to one of ordinary skill in the art, that the SR proteins also may be expressed in a variety of organisms including but not limited to *Saccharomyces cerevisiae,* filamentous fungi, and *E. coli.* Methods for expressing cloned genes in *Saccharomyces cerevisiae* are generally known in the art (see, "Gene Expression Technology," *Methods in Enzymology,* Vol. 185, Goeddel (ed.), Academic Press, San Diego, Calif., 1990 and "Guide to Yeast Genetics and Molecular Biology," *Methods in Enzymology,* Guthrie and Fink (eds.), Academic Press, San Diego, Calif., 1991; which are incorporated herein by reference).

Filamentous fungi (e.g., strains of Aspergillus) also may be used to express the proteins of the present invention. Methods for expressing genes and cDNAs in cultured mammalian cells and in *E. coli* is discussed in detail in Sambrook et al. (*Molecular Cloning: A Laboratory Manual, Second Edition,* Cold Spring Harbor, N.Y., 1989; which is incorporated herein by reference). As would be evident to one skilled in the art, one could express the protein of the instant invention in other host cells such as avian, insect and plant cells using regulatory sequences, vectors and methods well established in the literature.

Large scale suspension culture of cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

f. Purification of SR Polypeptides

Whether the SR protein is from a naturally derived source, a synthetic protein or produced from recombinatorial techniques, in certain embodiments, it will be desirable to produce purified compositions of the functional SR polypeptides or variants thereof. Protein purification techniques are well known to those of skill in the art. These techniques tend to involve the fractionation of the cellular milieu to separate the SR or related polypeptides from other components of the mixture. Having separated SR and related polypeptides from the other plasma components the SR or related polypeptide sample may be purified using chromatographic and electrophoretic techniques to achieve complete purification. Analytical methods particularly suited to the preparation of a pure peptide are ion-exchange chromatography, exclusion chromatography; polyacrylamide gel electrophoresis; isolectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a hepatocyte or β-cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% 60%, 70%, 80%, 90%, 95% or 99% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

D. Assays for the Detection of Autoimmune Disease

According to the present invention, there is provided a diagnostic application for the use of SR proteins. The present inventor has determined that certain antibodies against SR proteins are present in patients with autoimmune disease. While the present invention is exemplified in SLE, scleroderma, MCTD and APLS, its extension to other autoimmune disease listed herein above is contemplated. In preferred aspects of the present invention, an autoimmune disease may be detected using immunoassays and such immunoassays may be qualitative or quantitative.

The autoimmune disease may be detected by using the assay for SR antibodies individually or in combination with other diagnostic criteria for particular diseased states to provide a diagnostic evaluation of autoimmune disease. Accordingly, the assay for anti-SR antibodies may be used in combination with criteria such as facial erythema, discoid lupus rash, Raynaud's phenomenom, alopecia, photosensitivity, oral nasal or pharyngeal ulceration, arthritis without deformity, LE cells, false positive tests for syphilis, proteinurea (>3.5 g/day), pleuritis, pericarditis, psychosis, convulsions, hemolytic anemia, leukopenia and thrombocytopenia.

The detection may comprise monitoring the anti-SR antibodies in combination with a second, third, fourth, fifth, sixth, seventh eighth, ninth or tenth parameter such that each of the additional parameter is distinct from any other parameter used in combination with the anti-SR antibody.

As exemplified herein, an "SR antigen" may be defined by an alternating motif comprising a chain of phosphorylated acidic amino acid-basic amino acid dipeptide residues. More preferably the SR antigen comprises an alternating phosphorylated acidic amino acid/basic amino acid residues and still further preferred the SR antigen comprises a phosphoserine-arginine dipeptide or a phosphoserine-lysine dipeptide. In preferred embodiments, the SR antigen may be part of a full length SR protein or peptide or a synthetic polyepitopic molecule as described herein above. Thus, an anti-SR antibody as used herein is any antibody which is immunologically reactive with an SR antigen. In preferred embodiments, the SR antigens described herein are used to detect anti-SR antigen antibodies that are autoantibodies. In specific and preferred embodiments, these anti-SR antigen antibodies are present in autoimmune disease.

In a further embodiment, the present inventor's findings encompass diagnostic assays for determining the phosphate-sensitivity of patient autoantibodies. These assays can take the form of enzyme-linked immunosorbent assays, western blot assays, immunofluorescent assays and others described herein using any of the known antigens as the substrate. In one embodiment, the SR proteins, peptides or analogues of this invention are used as the substrates. Patients diagnosed as producing phosphatase-sensitive autoantibodies may then be assessed for a therapy to increase phosphatase activity or levels to decrease the presence of antigen in the patient. Thus, the present invention includes methods of treating patients with phosphate-sensitive autoantibodies with therapeutic agents that modulate phosphatase levels or activity. Such agents may be screened for the ability to specifically modulate phosphatase levels or may act to replace or supplement endogenous phosphatase activity. The assays of the present invention also may be used to monitor the level of phosphatase activity in the patient by measuring the concentration phosphate-sensitive antibodies.

a. Immunologic Detection of Autoimmune Disease

The present invention entails the use of SR antigens in the immunologic detection of anti-SR antibodies as a diagnostic for autoimmune disease. Various useful immunodetection methods have been described in the scientific literature, such as Nakamura et al. (1987; incorporated herein by reference). Immunoassays, in their most simple and direct sense, are binding assays. Certain preferred immunoassays are the various types of enzyme linked immunosorbent assays (ELISAs) and radioimmunoassays (RIA). Immunohistochemical detection using tissue sections also is particularly useful. However, it will be readily appreciated that detection is not limited to such techniques, and Western blotting, dot blotting, FACS analyses, precipitin reactions, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes. Preferred samples, according to the present invention, are fluids, such as milk, urine, blood, serum or saliva.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with SR antigens presented. After this time, the SR-antibody mixture will be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Pat. Nos. concerning the use of such labels include 3,817,837; 3,850,752; 3,939,350; 3,996,345; 4,277,437; 4,275,149; 4,302,534; 4,366,241; 4,637,988; 4,786,594; 5,108,896; 5,229,302; 5,629,164 and 5,691,154 each incorporated herein by reference. Of course, one may find additional advantages through the use of a secondary binding ligand such as a second antibody or a biotin/avidin ligand binding arrangement, as is known in the art.

Usually, the primary immune complexes may be detected by means of a second binding ligand that has binding affinity for the SR antigen or the SR-protein (antigen) specific antibody presented in the sample. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any unbound bound labeled secondary antibodies or ligands, and the remaining label in the secondary immune complexes is then detected.

Other methods include the detection of primary immune complexes by a two step approach. A second binding ligand, such as an antibody, that has binding affinity for the SR antigen or anti-SR antibody is used to form secondary immune complexes, as described above. The second binding ligand contains an enzyme capable of processing a substrate to a detectable product and, hence, amplifying signal over time. After washing, the secondary immune complexes are contacted with substrate, permitting detection.

Competitive immunodetection can also be used to detect the presence of antibodies specific for SR-antigens. In this technique, a labeled-antibody is first incubated in solution with the antigen. Signal emitted by the label is measured. This is followed, by contacting this antigen/antibody complex with a sample containing the antibodies of interest. If the sample has antibodies specific to the antigen, they will bind the antigen and competitively displace the labeled-antibody. This can be detected as a drop in intensity of the signal from the label.

Further, immunoassays employing antibodies and a fluorescer-quencher (F-Q) chromophoric pair, wherein one or both of the chromophoric pair are bonded to antibodies may be used for detection. Depending on the particular antigen(s) of interest, various reagent combinations can be employed, where the amount of quenching is directly related to the amount of antigen(s) present in the assay medium, i.e., the patient sera. In carrying out the assay, the sample and antibody specific for the antigen of interest, to which is bound one of the F-Q pair, are combined in an aqueous buffered medium. Depending on the protocol, different assay reagents are employed in the aqueous buffered medium: (1) antigen analog bonded to the other of the F-Q pair; (2) antibodies specific for the antigen to which is bound the other of the F-Q pair; or (3) a combination of a plurality of antigens bonded together through linking groups to a hub molecule, usually a polymer, in combination with antibody bound to the other of the F-Q pair. The composition is irradiated with light at a wavelength, absorbed by the fluorescing molecule and the amount of fluorescence determined. By employing appropriate standards, the presence and amount of the unknown antigen in the sample can be determined. These types of experiments are described, among others, in U.S. Pat. Nos. 3,996,345 and 5,229,302 incorporated herein by reference.

b. ELISA

As a part of the practice of the present invention, the principles of an enzyme-linked immunoassay (ELISA) may be used. ELISA was first introduced by Engvall and Perlmann (1971) and has become a powerful analytical tool using a variety of protocols (Engvall, 1980; Engvall, 1976; Engvall, 1977; Gripenberg et al., 1978; Makler et al., 1981; Sarngadharan et al., 1984). ELISA allows for substances to be passively adsorbed to solid supports such as plastic to enable facile handling under laboratory conditions. For a comprehensive treatise on ELISA the skilled artisan is referred to "ELISA; Theory and Practise" (Crowther, 1995 incorporated herein by reference).

The sensitivity of ELISA methods is dependent on the turnover of the enzyme used and the ease of detection of the product of the enzyme reaction. Enhancement of the sensitivity of these assay systems can be achieved by the use of fluorescent and radioactive substrates for the enzymes. There are also assays that employ clotting factors which involves coagulation, the enzyme-linked coagulation assay (ELCA as described in U.S. Pat. No. 5,071,745 EP 373908; and U.S. Pat. No. 6,468,621 each specifically incorporated herein by reference), discussed below. The assay involves coating microtiter plates with fibrinogen and adding enzyme labeled fibrinogen in solution. When thrombin is added the fibrinogen is converted to fibrin and the solution phase labeled fibrin binds to the solid phase unlabelled fibrin (U.S. Pat. No. 4,668,621 incorporated herein by reference).

Other immunoassays encompassed by the present invention include, but are not limited to those described in U.S. Pat. No. 4,367,110 (double monoclonal antibody sandwich assay) and U.S. Pat. No. 4,452,901 (Western blot). Other assays include immunoprecipitation of labeled ligands and immunocytochemistry, both in vitro and in vivo.

In a preferred embodiment, the invention comprises a "sandwich" ELISA, where SR antigens are immobilized onto a selected surface, such as a well in a polystyrene, bead, microtiter plate or test tube or a dipstick. The immobilization can be achieved by adsorption of the SR-antigen to the surface; non-covalent binding, for example, by binding of the antigen to an antibody attached to the surface; or by covalent means. Then, a test composition suspected of containing the anti-SR antibodies, e.g., a clinical sample, is contacted with the surface. After binding and washing to remove non-specifically bound immunocomplexes, the bound antigen may be detected by a second antibody to the anti-SR antibodies.

In another exemplary ELISA, SR polypeptides are immobilized onto a surface and then contacted with the anti-SR antibodies. After binding and washing to remove unbound immune complexes, the bound antibody is detected. In certain embodiments, it is envisioned that the SR-antigens may be bound to support through specific anti-SR antibodies. Where the initial SR antigens are linked to a detectable label, the primary immune complexes may be detected directly. Alternatively, the immune complexes may be detected using a second antibody that has binding affinity for the SR-specific antibody in the sample, with the second antibody being linked to a detectable label.

Another ELISA in which the anti-SR antibodies are detected involves the use of antibody competition in the detection. In this ELISA, labeled SR antigens are added to the wells, allowed to bind to the anti-SR antibodies, and detected by means of their label. The amount of anti-SR antibody in a sample is determined by mixing the sample with the labeled SR antibodies before or during incubation with coated wells. The presence of anti-SR antibodies in the sample acts to reduce the amount of SR antigen available for binding to the well, and thus reduces the ultimate signal.

Irrespective of the format employed, ELISAs have certain features in common, such as coating, incubating or binding, washing to remove unbound species, and detecting the bound immune complexes. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" or "blocked" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or clinical or biological sample to be tested under conditions effective to allow immune complex (antigen/antibody) formation. Detection of the immune complex then require a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG), evaporated or powdered milk, and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

To provide a detecting means, the second or third antibody will have an associated label to allow detection.

Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween). As will be evident to one skilled in the art, it may be desirable to dilute the sample with a suitable diluent to the assay.

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

A variant of ELISA is the enzyme-linked coagulation assay, or ELCA (U.S. Pat. No. 4,668,621), which uses the coagulation cascade combined with the labeling enzyme RVV-XA as a universal detection system. The advantage of this system for the current invention, is that the coagulation reactions can be performed at physiological pH in the presence of a wide variety of buffers. It is therefore possible to retain the integrity of complex analyses.

Another variant of a sandwich ELISA uses labeled anti-Fc antibodies directed against anti-SR antibodies. This allows for detection of a variety of antibody types in the serum tested. Antibodies or immunoglobulins (Igs) are composed of two heavy and two light chains, each of which contains an $NH_2$-terminal antigen-binding variable domain and a COOH-terminal constant domain responsible for the effector functions of antibodies. The COOH-terminal domains of Ig heavy chains form the Fc region. These regions are involved in triggering cellular activities through interaction with specific receptors known as Fc receptors (FcRs). Fc receptors for all Ig classes, or isotypes, (e.g., IgG (Fc.gamma.R), IgE (Fc.epsilon.R), IgA (Fc.alpha.R), IgM (Fc.mu.R) and IgD (Fc.delta.R) have been identified. Thus, Fc regions of antibodies are different with respect to Ig subtypes and hence, anti-Fc antibodies can be made against Fc regions specific to IgG, IgE, IgA, IgM and IgD antibodies, which allow the detection of antisera comprising of one or several of these antibodies.

C. Precipitin Reactions

Detection of large immunoprecipitates, such as those formed between polyepitopic antigens and antibodies, in aqueous solutions results in the formation of lattices between the antigenic determinants and antibodies, that develop into a visible precipitate (described in Kuby, 1994). The interaction of antigens with antibodies to form complexes occurs in minutes and formation of the visible precipitate follows. These precipitates develop as neighboring antibody molecules within the lattice form ionic bonds with each other, causing the lattice to loose its charge and thus become insoluble.

Formation of such lattices requires the antibody to be bivalent and the antigen to be bivalent or polyvalent, i.e., there must be at least two copies of the same epitope, or different epitopes that react with different antibodies present in polyclonal antisera.

The precipitin reactions can be used as a rapid detection test for the presence of antibodies to SR-antigens in patient sera. For this the antiserum is placed at the bottom of a tube and the antigen solution is carefully layered on top. If the antiserum contains the said antibodies, then antigens diffuse towards the antibodies and form a visible band of immunoprecipitate at the interface within a few minutes.

Radial immunodiffusion. Typically, a suitable dilution of the antibody is incorporated into a gel and the antigen is placed in a well and allowed to diffuses into the agar. As the antigen binds antibodies in the gel, lines of visible immunoprecipitates are formed.

Double immunodiffusion. In this method, both antigen and antibody diffuses radially towards each other from wells, establishing a concentration gradient. As equivalence is reached, a visible immunoprecipitin line is seen.

Precipitin reactions can be performed in liquid or semi-sold media such as agar gels. These methods may be used in combination with immunoelectrophoresis to allow even faster detection rates.

d. Immunohistochemistry

While primarily useful in research contexts, immunohistochemistry may be useful according to the present invention in identifying autoimmune disease. Such a detection method would require a biopsy of a sample from an individual suffering from an autoimmune disease. This technique involves testing of both fresh-frozen and formalin-fixed, paraffin-embedded tissue blocks prepared from study by immunohistochemistry (IHC). For example, each tissue block consists of 50 mg of residual "pulverized" tissue. The method of preparing tissue blocks from these particulate specimens has been successfully used in previous IHC studies of various diagnostic and prognostic factors, e.g., in breast, and is well known to those of skill in the art (Brown et al., 1990; Abbondanzo et al., 1990; Allred et al., 1990).

Briefly, frozen-sections may be prepared by rehydrating 50 ng of frozen "pulverized" sample at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 intact cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

e. Western Blots

The compositions of the present invention will find great use in immunoblot or western blot analysis. The SR antigen composition may be used as high-affinity primary reagents for the identification of anti-SR antibodies immobilized onto a solid support matrix, such as nitrocellulose, nylon or combinations thereof. Immunologically-based detection methods for use in conjunction with Western blotting include enzymatically-, radiolabel-, or fluorescently-tagged secondary antibodies against the SR antigens are also considered to be of particular use in this regard.

Enzyme-linked immunoelectrotransfer blotting techniques are often used in the identification of antibodies to known antigens. For example, U.S. Pat. No. 5,320,940 (specifically incorporated herein by reference) describes the use of Western blots to identify antibodies to HIV-related antigens to aid in the diagnosis of autoimmune disease. In Western Blot assays antigens are blotted onto a nitrocellulose membrane. The antigens can either be in a pure form and placed onto a nitrocellulose as a distinct dot (dot-blot), or alternatively the antigens may be resolved using techniques such as SDS-PAGE prior to transfer to the nitrocellulose membrane. The nitrocellulose membrane is then incubated with an antibody containing sample such as serum sample, from the individual suspected of having the autoimmune disease. The immunoglobulins specifically bound to the SR antigens can then be visualized by reactions with goat anti-human IgG conjugated to a detectable label. In a particular example, the goat anti-human IgG is conjugated to biotin and a series of reactions using avidin conjugated to horseradish peroxidase and an HRP specific substrate result in the visualization of the SR bound antibodies.

f. Monitoring Disease Progression

In practice, the amount of anti-SR autoantibodies in the patient available to bind to SR antigens may be monitored, such as by the procedures described herein above, on a repeated basis to monitor the progression or state of the disease, or effectively carry out a therapeutic treatment. This may be carried out by collecting the biological sample at intervals of from about one week to one month, preferably weekly, from the subject, so that the increase or decrease in autoantibody levels in the subject over time may be seen. A decrease in the autoantibodies indicates improvement or a possibility of improvement in the disease, and an increase in the autoantibodies indicates progression or risk of progression of the disease. Typically, where monitoring is carried out in conjunction with a treatment of the disease, at least one measure will be taken from the subject to confirm the autoimmune basis of the disorder prior to initiating treatment, and preferably several measures will be taken to establish a baseline titer or amount of the autoantibody in the subject. The antibody measure is then to be taken at least periodically after the therapeutic intervention, and the condition of the patient monitored by standard clinical indices, to determine the efficacy of the therapeutic treatment and adjust the treatment to enhance the efficacy thereof.

E. Immunodetection Kits

In further embodiments, the invention provides immunological kits for use in detecting anti-SR antibodies in biological samples. Such kits will generally comprise one or more SR antigens that have will likely produce an immunoreaction for various anti-SR antibodies. More specifically, the immunodetection kits will thus comprise, in suitable container means, one or more SR antigens, antibodies that bind to SR antigens, antibodies that bind to other antibodies via Fc portions and antibodies that bind to anti-SR antibody variable regions, so called "anti-Id" antibodies.

In certain embodiments, the SR antigen or secondary anti-SR antibody may be provided bound to a solid support, such as a column matrix or well of a microtiter, beads, dipsticks plate. Alternatively, the support may be provided as a separate element of the kit.

The immunodetection reagents of the kit may include detectable labels that are associated with, or linked to, the given detecting antibody or to the SR antigen itself. Detectable labels that are associated with or attached to a secondary binding ligand are also contemplated. Such detectable labels include chemilluminescent or fluorescent molecules (rhodamine, fluorescein, green fluorescent protein, luciferase), biotin, radioabels ($^3$H, $^{35}$S, $^{32}$p, $^{14}$C, $^{131}$I) or enzymes (alkaline phosphatase, horseradish peroxidase).

The kits may further comprise suitable standards of predetermined amounts, including both antibodies and SR antigens. These may be used to prepare a standard curve for a detection assay.

The kits of the invention, regardless of type, will generally comprise one or more containers into which the biological agents are placed and, preferably, suitable aliquoted. The components of the kits may be packaged either in aqueous media or in lyophilized form.

The compositions of the present invention may be advantageously packaged into a kit comprising the active reagent (s) a suitable container means and even instructions for use of said kit. The reagent(s) of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

The container means of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed.

The kits of the present invention also will typically include a means for containing the antibody, SR antigen and any other reagent containers in close confinement for commercial sale. Such containers may include injection or blow-molded plastic containers into which the desired vials are retained.

F. Tolerization and Pharmaceuticals

Immune tolerance is an immunological non-responsiveness induced against selected antigen(s) by a previous exposure to the same antigen or antigenic determinant, usually in a modified form or dose. Tolerance to self antigens occurs in part due to deletion of self-reactive T-cells in development in the thymus. Breakdown of this clonal deletion is one mechanism in which autoimmune disease results. Thus, it is contemplated that tolerance may be an effective mechanism of ameliorating the effects of autoimmune disease. Such a technique would be especially useful in individuals with a genetic or other predisposition to autoimmune disease.

Oral tolerance, is a classic technique for inducing immune tolerance (Weiner, 1993; Chase, 1946), and may be employed to reduce the amount of anti-SR antigen autoantibodies in a subject having an autoimmune disease. Such techniques may involve orally administering to the subject an active agent comprising an SR protein as described above, or an antigenic fragment thereof or fusion protein of either thereof. This produces an alteration of the immune response to the antigen which may suppress a previous immune response to that antigen. An immune adjuvant (e.g., a lipopolysaccharide) may optionally be administered concurrently with the antigen.

Depending on the species and nature of active agent, whether or not an adjuvant is administered, the condition of the subject, and the schedule of administration, the oral dosage of the active agent may be administered in any amount effective to achieve oral tolerance. A non-limiting example of dosage is from about 10 or 20 mg up to about 500 or 1000 mg of SR antigenic composition. The dosage may be administered in accordance with any suitable schedule, such as one, two, or three times daily.

Formulations useful for carrying out oral tolerance treatments as described above comprise an active agent as described above, typically in combination with an orally administrable carrier, in an orally administrable form. Orally administrable formulations may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier. In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active agent, optionally with one or more accessory ingredients such as an immune adjuvant.

The compositions used for tolerization also may be formulated for parenteral systemic administration to the host. The tolerization compositions for parenteral administration, may be subcutaneously, intramuscularly, or intravenously administered. Thus, the present invention provides compositions for administration to a host, where the compositions comprise a pharmaceutically acceptable solution of the identified compound in an acceptable carrier, as described above. Typically, injectibles are prepared either as liquid solutions or suspensions; solid forms suitable for using to prepare solutions or suspensions upon the addition of a liquid prior to injection can also be prepared; and the preparations can also be emulsified.

The tolerization compositions suitable for injectible use may include sterile aqueous solutions or dispersions; formulations including sesame oil, peanut oil or aqueous propylene glycol; and sterile powders for the extemporaneous preparation of sterile injectible solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Sterile injectible solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectible solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for local injection also is contemplated. In this regard, the use of DMSO as solvent is preferred as this will result in extremely rapid penetration, delivering high concentrations of the active agents to a small area.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms The pharmaceutically acceptable carrier can be any compatible, non-toxic substance suitable to deliver the compounds to an intended host. The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectible compositions can be brought about by the use in the compositions of agents delaying absorption, for example, aluminum monostearate and gelatin.

Pharmaceutically acceptable adjuvants, buffering agents, dispersing agents, and the like may also be incorporated into the tolerization compositions. Preparation of pharmaceutical compositions incorporating active agents is well described in the medical and scientific literature. See, for example, Remington's Pharmaceutical Sciences, Mack Publishing Company, Easton, Pa., 16th Ed., 1982, the disclosure of which is incorporated herein by reference. Dosages may vary according to the physician's diagnosis and the route of administration chosen. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580).

Under ordinary conditions of storage and use, the injectible preparations may further contain a preservative to prevent growth of microorganisms. Intravenous vehicles include fluid and nutrient replenishers. Preservatives include antimicrobial agents, anti-oxidants, chelating agents and inert gases. The pH and exact concentration of the various components in the tolerization composition are adjusted according to well-known parameters.

Upon formulation, solutions will be administered in a manner compatible with the dosage formulation and in such amount as is diagnostically or therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In other embodiments, direct injection into the thymus is contemplated. Finally, systemic administration may be performed. Continuous administration also may be applied where appropriate. Delivery via syringe or catherization is also contemplated.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

A. Purification and Microsequencing of SR Proteins

Protein purifications were carried out as described in Zahler et al., 1992, and are incorporated herein by reference. The purification was started with $1\times10^{10}$ HeLa cells or 100 grams of calf thymus. Cells and tissues were ground to a fine powder in Liquid $N_2$ using a mortar and pestle. The powder was then transferred to a beaker on ice, and 350 ml of isolation buffer was added (isolation buffer is 65 mM KCl, 15 MM NaCl, 10 mM HEPES at pH 7.6, 10 mM $Na_2$ EDTA, 5 mM potassium fluoride (KF), 5 mM β-glycerophosphate, 0.2 mM PMSF, and 2 μg/ml of aprotinin). Tissue culture cells were sonicated 10 times for 20 sec with a probe sonicator set at 50 W; thymus was sonicated continuously for 20 min. Homogenates were centrifuged for 20 min at 8000×g, supernatants were transferred to a beaker, and ammonium sulfate was added to 65% of saturation. After 2 h of stirring at 4° C., the extract was centrifuged at 8000×g for 20 min. Supernatants were transferred to clean tubes and centrifuged again at 8000×g for 20 min. Supernatants were collected, and ammonium sulfate was added to 90% of saturation. Extracts were stirred at 4° C. for 0.5–12 h followed by centrifugation at 25,000 rpm (8,500×g) in an SW28 rotor at 4° C. for 1 h. Supernatants were removed, and pellets were rinsed with 90% ammonium sulfate in isolation buffer. Pellets were resuspended in 10 ml of dialysis buffer (65 mM KCl, 15 mM NaCl, 10 mM HEPES at pH 7.6, 1 mM $Na_2$ EDTA, 2 mM DDT, 5 mM KF, 5 mM β-glycerophosphate, and 0.2 mM PMSF) and dialyzed against three changes of 1.4 liter of dialysis buffer over the course of 16 h. The dialysate was recovered and stored in 1.0-ml aliquots at −80° C.

Dialysate aliquots were thawed and centrifuged for 15 min at 13,000×g. Supernatants were transferred to clean tubes, and $MgCl_2$ was added to 20 mM. After a 1 h incubation on ice, tubes were centrifuged at 13,000×g for 30 min. After removal of supernatants, the pellets were washed with 200 μl of 20 mM $MgCl_2$ dialysis buffer and resuspended in 20 μl of 5% glycerol buffer D (Dignam et al., 1983, incorporated herin by reference). Resuspended pellets containing the purified SR proteins were transferred to clean tubes.

Immunoblotting with mAB104 was performed according to methods published previously (Roth et al., 1991, incorpotated herin by reference).

B. Trypsin Digestion, HPLC Separation and Microsequencing of SR Proteins

Purified SR proteins were separated by SDS-PAGE and electro-transferred to nitrocellulose membrane. Individual SR protein bands were excised and submitted to in situ digestion with trypsin (Aebersold et al., 1987), omitting the NaOH wash. The resulting peptide mixture was separated by narrow-bore HPLC chromatography using a Vydac C18 2.1×150 mm reverse-phase column on a Hewlett-Packard 1090 HPLC/1040 diode array detector. Optimum fractions from each peptide chromatogram were chosen on the basis of differential UV absorbance at 210, 277 and 292 nm, peak symmetry, resolution, and column retention time. Automated Edman degradation was performed on an Applied Biosystems 477A protein sequencer by standard methods, except that the reaction cartridge temperature was raised to 53° C. during coupling with a commensurate decrease in R2 delivery and dry-down times. Details of strategies for the selection of peptide fractions and their microsequencing have been described (Lane et al., 1991).

C. Isolation of a cDNA Encoding hSRp20

Oligonucleotides corresponding to the sequence immediately before the start codon of X16 and the reverse complement of the sequence immediately after the X16 stop codon were used to prime the synthesis of hSRp20 cDNAs from a mixture of cDNAs prepared from total HeLa RNA (Rupp and Wentraub, 1991). The cDNAs were separated by agarose gel electrophoresis and identified by ethidium staining. The 530-bp cDNA was inserted into BS/KS+, and both strands were sequenced using the dideoxy method (Sanger et al., 1977).

D. Separation of Purified SR Proteins $MgCl_2$ pellets of 65–90% ammonium sulfate extracts from 150 grams of calf thymus were resuspended in 5% glycerol buffer D (Dignam et al., 1983) as described above. An equal volume of sample buffer (4% SDS, 125 mM Tri-Cl at pH 6.8, 20% glycerol, 10% β-mercaptoethanol) was added, and the proteins were separated by SDS-10% PAGE. Proteins were eluted from the gel by the methods of Hager and Burgess (1980), with several modifications. Proteins bands were visualized by soaking the gel in 0.25 M KCl at 4° C. for 5 min. Bands were cut from the gel with a razor, soaked in $dH_2O$ for 5 min, and ground to a fine powder under liquid $N_2$ with a mortar and pestle. The powder was then transferred to an Eppendorf tube, along with 500 μl of protein gel elution buffer (0.1% SDS, 50 mM Tris-Cl at pH 8.0, 0.1 mM EDTA, 5 mM DDT, 0.15 M NaCl) and 5 μl of 10 mg/ml acetylated bovine serum albumin (BSA) (New England Biolabs). Proteins were eluted by rocking at room temperature overnight. The acrylamide was removed by centrifugation, and the supernatant was transferred to a clean tube. This was repeated three to five times to ensure that all of the acrylamide fragments were removed. Four volumes of acetone at −20° C. were added to the supernatant, and the tubes were incubated on dry ice for 30 min. Samples were centrifuged at 13,000×g for 20 min, and the supernatant was thoroughly removed without allowing the pellet to dry. Pellets were resuspended immediately in 5 μl of 6.0M guanidine-HCl in buffer D and incubated at room temperature for 20 min. Buffer D (250 μl) was then added to each tube, and the proteins were renatured at room temperature for 1 h. $MgCl_2$ was added to a final concentration of 20 mM, and the tubes were incubated on ice for 1 h. SR protein aggregates were removed by centrifugation at 13,000×g for 30 min as described above. Sedimented 40 kD 55 kD, and 70 kD SR proteins were resuspended in 40 μl of 5% glycerol buffer D; the 30-kD SR protein was resuspended in 100 μl.

E. Proteins and Antibodies

SR proteins were purified to homogeneity from exponentially growing HeLa cells by methods described in Zahier et al. (1992; 1993). SR proteins were dephosphorylated with calf intestinal alkaline phosphatase (Boehringer-Mannheim, Ind.) as described (Zahier et al., 1993). RE-GST protein, a fusion between glutathione-S-transferase and an alternating-arginine sequence, KDRKDRERERERERRERERERER-EREKEKERERDRERNSE (SEQ ID NO:1), that serves as an epitore for mAb 16H3 against SR proteins and U1 70K, was produced in *E. coli* and purified by standard procedures on a glutathione agarose column (Neugebauer et al., 1995). Cells secreting the Y12 mAb against the Sm epitope are described in Petterson et al. (1984).

F. Patient Sera

All patients with definite or suspected systemic lupus, lupus-like syndromes, or primary antiphospholipid syndrome, who attended rheumatology clinics or private practice at St. Luke's/Roosevelt Hospital center, New York, N.Y., or who were identified as possible subjects through the Saint Vincent's Medical Center, New York, N.Y., were asked to participate in these studies. Blood specimens were obtained from those who completed the informed consent process. Medical records were reviewed to confirm diagnostic categories and sera and plasma were tested for antibodies to phospholipid plus β2-glycoprotein I and to purified β2-glycoprotein I. Patients were defined as having systemic lupus if they could be documented to meet at least four 1987 ACR criteria (i.e. criteria set by the American College of Rheumatology for systemic lupus), confirmed by history, examination and/or medical records. Patients were considered to have antiphospholipid syndrome if they met both of the required criteria: 1) Positive test for antiphospholipid antibodies and/or antibodies to purified β2-glycoprotein I and/or lupus anticoagulant; 2) History of mid-term to late pregnancy loss and/or at least one major thrombotic episode including deep venous thrombosis, cerebrovascular accident, or another documented venous or arterial occlusion. Minor criteria for antiphospholipid syndrome, such as thrombocytopenia or livedo reticularis were considered confirmatory but not diagnostic of this category. Non-immune sera were collected at the University of Washington from clinically unaffected individuals and were not pre-selected to be negative for other markers.

G. ELISA Assay

Ninety-six-well immunoplates (Nunc) were coated overnight at 4° C. with 0.1 ml per well 0.5–2.0 mg/ml SR proteins resuspended in 10 mM EDTA in PBS. Alternatively, plates were coated with 5 mg/ml RE-GST in PBS. After washing with TBST (50 mM Tris-HCl pH 8.5, 180 mM NaCl, 0.1% Tween-20), the plates were blocked with 3% BSA (Sigma, Fraction V) in TBST for 1 h at room temperature. The blocking solution was removed and antisera added by diluting in blocking solution to final concentrations as indicated. All patient sera were numerically coded and tested in a "blind" fashion. After 1 h incubation at RT, the plates were washed three times with TBST and bound antibody was detected using biotinylated anti-human IgG followed by HRP-streptavidin (Vector Labs, Burlingame, Calif.). HRP was reacted with the TMB system (KPL) and development was stopped by the addition of 1 M phosphoric acid. The stabilized reaction product was quantified, by reading the absorbance at 450 nm in a plate reader (Bio-Rad Laboratories, Hercules, Calif.).

H. Western Blotting

Approximately 0.25 mg of purified human SR proteins were run on 10% SDS-polyacrylamide gels. Gels were transferred to PVDF membrane (Micron Separations Inc., Westborough, Mass.) or nitrocellulose (Schleicher and Schuell, Keene, N.H.), stained with Ponceau S, blocked for 10 min at RT in 3% BSA in TBST (50 mM Tris-HCl pH 8.0; 150 mM NaCl; 0.05% Tween 20) or 1% PVA (0.05% Tween 20, PBS), and incubated for 1 h at RT in primary antibody diluted 1:250 in blocking solution. Blots were then washed 3 times in TBST and processed for ECL (Amersham Corp., Arlington Heights, Ill.) detection using the Vectastain ABC kit (Vector Labs, Burlingame, Calif.).

Example 2

Results & Discussion

Results

To determine whether SR proteins are autoantigens in any of a variety of diseases, an ELISA assay was developed. Human SR proteins were purified to homogeneity from HeLa cells grown in suspension and used to coat immunoplates at concentrations ranging from 0.5 to 2 mg/ml. At these coating concentrations, a monoclonal antibody (mAb) specific for the SR protein family, mAb1H4 (Neugebauer and Roth, 1997), gives a robust signal in the ELISA assay. In contrast, mAb Y12 against the Sm epitope gives no signal above background, indicating that the SR protein preparation is not detectably contaminated with snRNPs.

Figure 3:
FIG. 3. The presence of autoantisera against SR proteins at a 1:200 dilution in sera from patients with SLE, APLS and MCTD.

The inventor performed an ELISA assay for SR protein reactivity on sera obtained from patients with SLE, APLS, MCTD, PSS and Sjorgens syndrome. FIG. 2 and FIG. 3 show the presence of autoantisera against SR proteins at a 1:50 dilution and 1:200 dilution respectively. These data provide clear evidence of the presence of anti-SR protein antibodies in patients with SLE, APLS, PSS and MCTD but not Sjorgens syndrome.

Figure 4A:
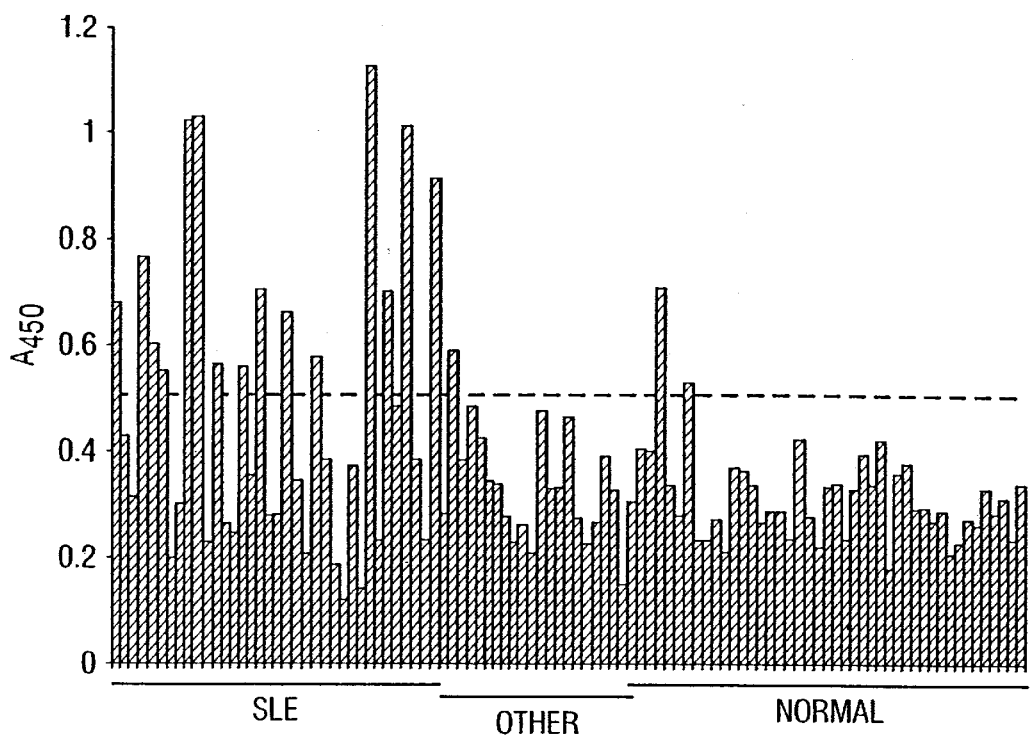
FIGS. 4A–B. Autoimmune patients react with SR proteins but not RE-GST in the ELISA.

An ELISA assay for SR protein reactivity was initially performed with 58 test patient sera and 44 normal sera, and quantitated reactivity using a plate reader (see Example 1: Materials and Methods). The test patient sera were representative of a variety of autoimmune disorders (see Table 3 for listing). The identity of the patients' respective diseases were not revealed to the investigators performing the ELISA until after the data was collected. FIG. 4 shows that a significant number of patients had high antibody titers for SR proteins relative to the normal controls. Using a criterion of two times the standard deviation plus the normal mean, the inventor determined that 16 of the 58 patient sera reacted with SR proteins. Of these 16 patients, 15 had SLE and 1 had mixed connective tissue disorder (MCTD). Sera from patients with rheumatoid arthritis (RA, n=2) and Sjogrens syndrome (n=4) did not react. Thus, among the diseases first examined, SLE showed the greatest number of positive patients. Two (5%) of the normal sera had significant antibody titers, reflecting the 2 standard deviation cutoff of a normally distributed data set (95% of the data points should fall within 2 standard deviations). The scores of the two positive normal sera were between 2 and 3 standard deviations above the mean. The fluctuation in titers present in the normal population is reminiscent of the finding that up to 30% of the normal population has positive ANA titers, depending on how the assay is conducted (Tan et al., 1997).

TABLE 3

| Disease | Number of Patients | Number Positive |
| --- | --- | --- |
| SLE | 37 | 16 |
| SLE with APLS | 11 | 5 |
| APLS | 1 | 1 |
| MCTD | 3 | 1 |
| Rheumatoid arthritis | 6 | 1 |
| Sjogren's syndrome | 6 | 0 |
| Eosinophilic fascitis | 2 | 0 |
| Vasculitis | 2 | 0 |
| Chronic fatigue syndrome | 4 | 1 |
| Scleroderma | 3 | 0 |
| Crest | 2 | 0 |
| Hyperprolactinemia | 2 | 1 |
| Osteoarthritis | 1 | 0 |
| Churg-Strauss syndrome | 1 | 0 |
| Idio. thrombo. purpura | 1 | 0 |
| Hashimoto's thyroiditis | 1 | 0 |
| Fibromyalgia | 2 | 2 |

TABLE 3-continued

| Disease | Number of Patients | Number Positive |
|---|---|---|
| Diabetes | 1 | 0 |
| Myopathy | 1 | 0 |
| Parvo virus arthritis | 1 | 0 |

Table 3. Results of a double-blind ELISA test of a group of 90 patient sera from patients with a variety of autoimmune disorders. ELISA test scores were considered positive if they were greater than or equal to the mean +/− 2 times the standard deviation of the normal group.

Because SR proteins are related to the U1 70K protein through their highly charged alternating-arginine domains (Neugebauer et al., 1995), the inventor assessed whether the SR-positive sera also would bind any alternating arginine domain. The same patient sera were subjected to ELISA with RE-GST, a glutathione-S-transferase fusion protein containing an alternating arginine sequence and recognized by mAb 16H3 against the SR proteins as well as U1 70K (see Example 1: Materials and Methods). None of the patient sera that had reacted with SR proteins gave signals greater than 2 standard deviations above the normal mean. Two sera from the normal pool reacted. Only one patient serum reacted with RE-GST, and that patient had Sjogren's syndrome. Therefore, bacterially expressed RE-GST cannot substitute for SR proteins in the ELISA of patient sera.

Figure 4B:
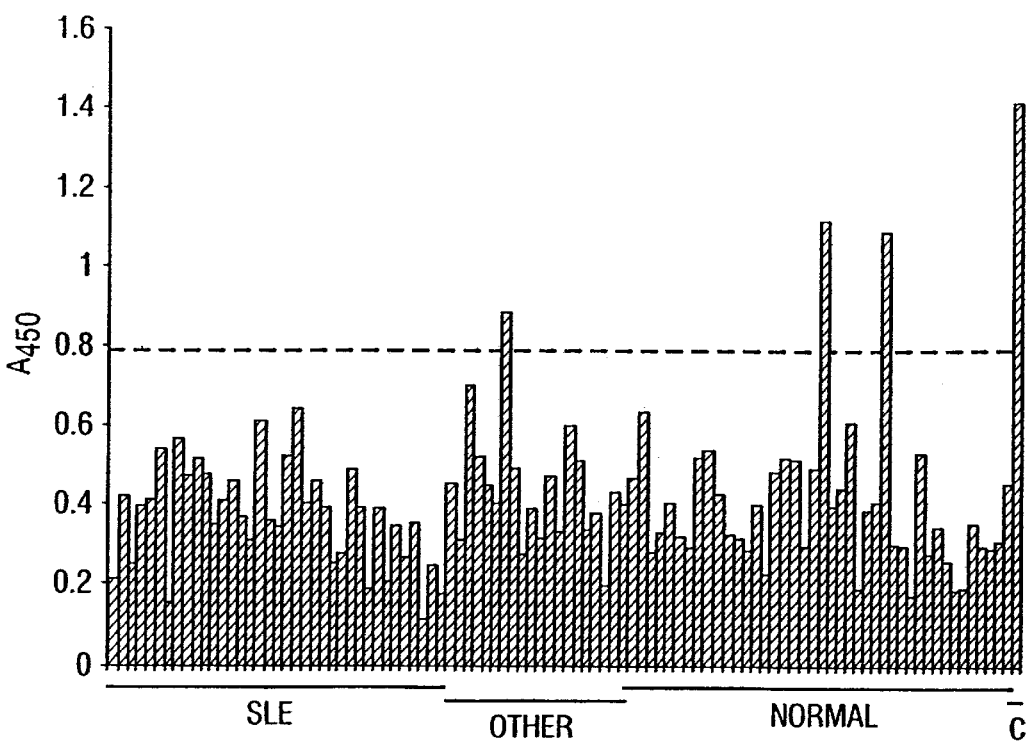

To expand the inventor's initial analysis, an additional 33 patients were tested for reactivity with SR proteins in the ELISA assay described herin, and combined with the results with those from FIG. 4 in Table 3. Of a total of 48 SLE patients, 21 (44%) reacted strongly with SR proteins. The positive scores ranged from 2 to 8 standard deviations above the normal mean. Included in the study were 11 SLE patients whose sera also had antiphospholipid antibodies (APLA), and of these, 5 (46%) reacted with SR proteins. A single patient with primary APLS was positive. Among the 39 patients with autoimmune disorders distinct from SLE, 6 (15%) reacted: 1 of 3 MCTD, 1 of 6 RA, 1 of 4 chronic fatigue syndrome (CFS), 1 of 2 hyperprolactinemia, and 2 of 2 fibromyalgia (see Table 3). Consistent with the results presented in FIG. 4B, no further patient sera reacted with RE-GST.

Figure 5:
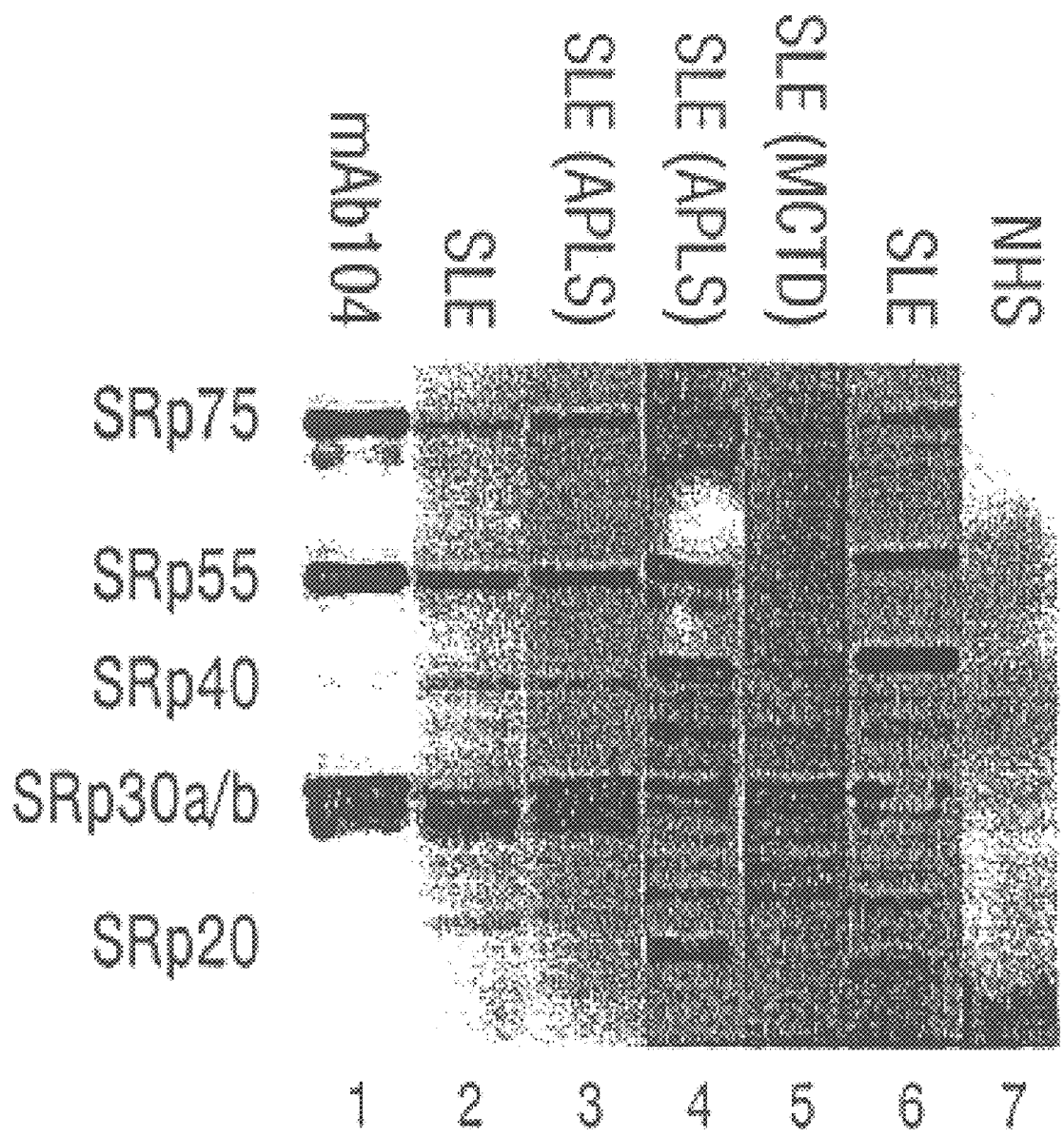
FIG. 5. Patient sera react directly with members of the SR protein family. Representative patient sera (diluted to 1:250 in blocking solution) were tested for reactivity with purified human SR proteins by immunoblotting. Lane 1 shows SR proteins as recognized by mAb104 which reacts with an epitope shared by all family members. Both patients with APES also have SLE.

To demonstrate reactivity of patient sera with SR proteins themselves, and further exclude the possibility that the SR protein preparation was contaminated with either DNA or snRNPs, the inventor performed immunoblotting with a number of patient sera. FIG. 5 shows that all five positive antisera tested recognized SR protein bands. Lane 1 shows the canonical SR proteins recognized by mAb 104 which binds a common phosphoepitope present in the SR domain of all SR proteins (Zahler et al., 1992; Zahler et al., 1993). All SR protein species were bound by antisera from patients with SLE (lanes 2, 3, 4, and 6). Interestingly, different sera seemed to bind preferentially to different SR protein family members; for example, the sera used in lanes 4 and 6 react more strongly than do the other sera, and SRp30a/b was the predominant antigen in the serum from the one SR-reactive MCTD patient (lane 5). These results confirm that the autoepitopes are resident on the SR protein polypeptides themselves.

Figure 6A:
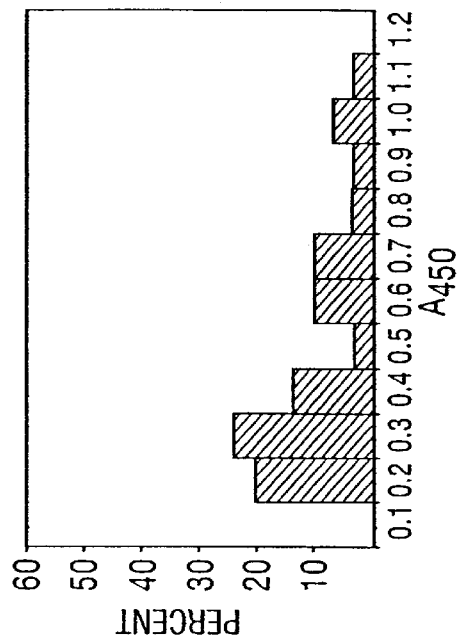
FIGS. 6A–D. Frequency histograms showing the reactivity of normal sera and four sets of patient sera with SR proteins. Following the assay which was performed double-blind, the sera were grouped according to whether the patients were diagnosed with SLE by 1987 ACR criteria and/or showed anti-phospholipid reactivity (APLA).
Figure 6B:
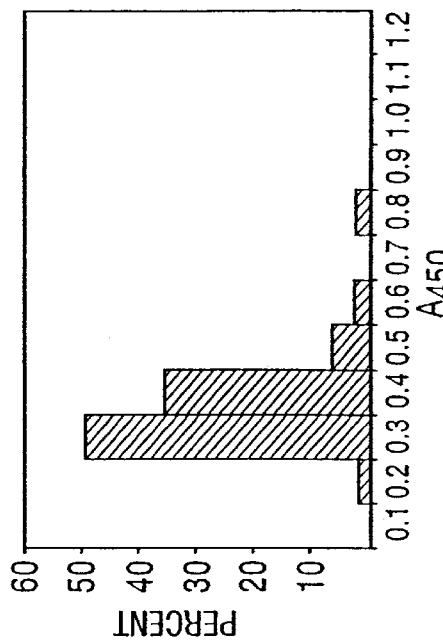
Figure 6C:
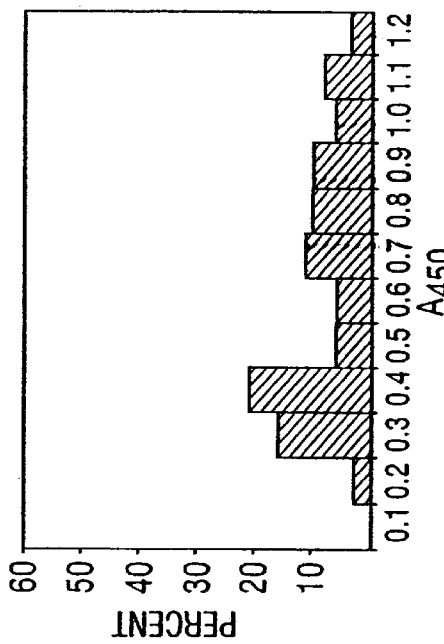
Figure 6D:
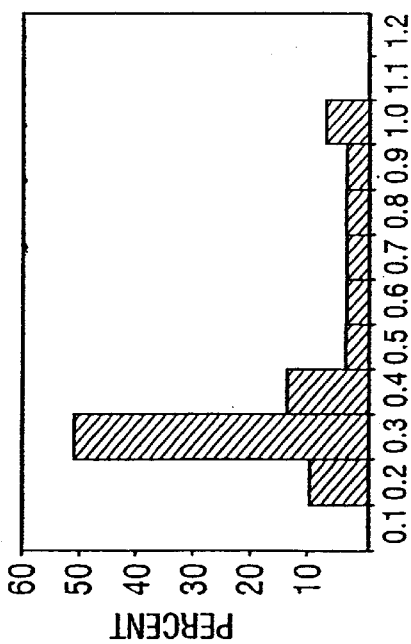

Because 5 of 11 patients with SLE and APLS and 1 of 1 patient with primary APLS were positive for SR protein reactivity in the initial assay (see Table 3), the inventor further examined the association of SR reactivity with primary APLS. APLS has emerged as a primary thrombophilic syndrome of its own and is characterized by antiphospholipid antibodies (APLA) and a high incidence of clotting disorders (Harris, 1989; Alarcon-Segovia and Sanchez-Guerrero, 1989; Asherson et al., 1989; Lockshin, 1994; Khamashta and Hughes, 1995). Three groups of patients were compared to the normal group: a) 63 sera from patients with SLE and APLA, b) 39 sera from patients with SLE but not APLA, and c) 29 sera from patients with primary APLS. FIGS. 6A–C shows the frequency distributions for each of these groups anti-SR ELISA scores compared to the normal group (d). Both SLE distributions (a and b) are significantly skewed from the normal group. Some skewing is evident in the group with primary APLS (c), due to the positivity of a very limited number of patients. Table 4 shows that the average anti-SR scores are highest for the groups with SLE, while the large standard deviations indicate the great variety within those groups. Using the 2 standard deviation above the normal mean as a criterion for positivity, the data in Table 4 supports the conclusion that SR autoreactivity correlates best with SLE and APLA (59% positive), followed by SLE alone (36%) and then by primary APLS (19%). These numbers differ somewhat from the results obtained from the first group of patients (see Table 3) in which 46% of patients with both SLE and APLA and 43% of patients with only SLE reacted. As these patient groups were obtained from different sources, this variation may reflect different populations represented by the two groups.

Figure 7:
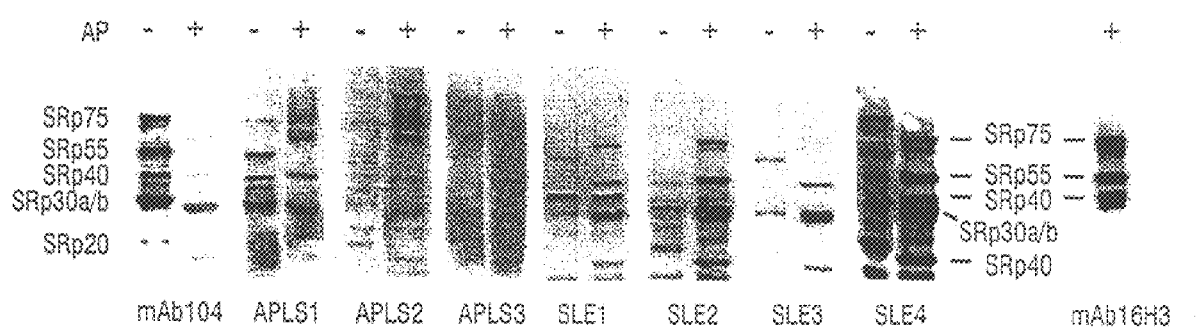
FIG. 7. Patient sera reactivity with native or enzymatically dephosphorylated SR proteins. Lanes containing proteins treated with alkaline phosphatase (AP) are indicated with − and +. mAb104 reactivity is dependent on the presence of phosphates (left), whereas mAb 16H3 binds dephosphorylated SRp75, SRp55, and Srp40, but NOT SRp30a or b (right). Patient sera APLS1, APLS2, and APLS3 are from patients who have primary APLS and were positive in the SR ELISA test (see FIG. 6C). Sera SLE1 and SLE4 were classified as having SLE only from the original clinical samples (Table 3); SLE2 and SLE3 sera also have APLA and were positive in the test shown in FIG. 6A.

In an effort to better understand the nature of the autoepitopes recognized by the sera from these patient groups, the inventor subjected purified SR proteins to enzymatic dephosphorylation which is known to remove the phosphate-dependent epitopes recognized by mAb104 (FIG. 7; Zahler et al., 1993). Upon immunoblot analysis with SR-reactive sera from patients with either primary APLS or SLE, it was found that the reactivity of most sera with SR proteins was highly dependent upon the presence of phosphates. In one case, the loss of phosphates abolished immunoreactivity (APLS1); however, in four other cases, immunoreactivity significantly increased upon dephosphorylation. For example, APLS2 reacted poorly with phosphorylated SR proteins, but showed some specificity for the dephosphorylated form of SRp75. In the case of SLE4, immunoreactivity was apparently equivalent between the phosphorylated and dephosphorylated SR proteins. Patient serum APLS3 did not react with SR proteins at all on immunoblot despite the fact that this serum was positive on the ELISA test shown in FIG. 6. This serum likely recognizes a discontinuous epitope on SR proteins. These striking results suggest that the circulating antibodies in each of these patients are fairly limited in the number of SR protein epitopes they bind.

TABLE 4

| Group | SLE | APLA | Anti-SR | n | % positive |
|---|---|---|---|---|---|
| a | yes | yes | 0.614 +/− 0.309 | 63 | 59 |
| b | yes | no | 0.437 +/− 0.280 | 39 | 36 |
| c | no | yes | 0.361 +/− 0.235 | 29 | 19 |
| d | no | no | 0.315 +/− 0.092 | 44 | 5 |

Table 4. Results of a double-blind ELISA test of a group of 121 patient sera from patients with SLE and/or APLS.The mean and standard deviation of the ELISA scores are shown and the percent of patients reactive with SR proteins is shown. Scores were considered positive if they were greater than or equal to the mean of the normal group (n = 44) + 2 standard deviations. The other groups -- a) 63 patients with SLE and APLA, b) 39 patients with SLE but without APLA, and c) 29 patients with primary A a history of clotting but without SLE) -- correspond with the groups presented in FIG. 6. (d) the normal group of 44.

Discussion

The results presented here show that members of the SR protein family of splicing factors are targets in autoimmune disease. The inventor developed an ELISA assay with purified SR proteins and tested a group of 90 patients with a variety of autoimmune disorders. A striking correlation emerged between anti-SR reactivity and SLE: 44% of SLE patients had titers of anti-SR immunoreactivity greater than 2 standard deviations from the normal mean. Patients with other autoimmune disorders, such as rheumatoid arthritis and Sjogren's syndrome, did not have significant titers for anti-SR. In a distinct study of 121 patients with SLE and/or APLS, the inventor found that patients with primary APLS reacted with SR proteins infrequently (19%); the group with the highest rate of reactivity with SR proteins (59%) was SLE patients who also had APLA.

SR proteins were shown to be autoantigens by ELISA and immunoblots with purified human SR proteins. Patient sera reactivity was not due to snRNP contamination, because antibodies against the Sm epitope did not react with the inventor SR protein preparation in the ELISA. Moreover, the molecular weights of the immunoreactive protein bands in the immunoblots were consistent with SR protein family members. Thus, the SR protein polypeptides themselves or post-translational modifications of those peptides contain the autoepitopes. In addition, the SR protein preparation yields protein that is highly purified from contaminants as assessed by Coomassie blue staining (Zahler et al., 1993), making it unlikely that contaminant molecules would be abundant enough to account for some of the patient sera signals in the ELISA. The present results demonstrate that SR proteins are direct antigens in SLE. Since many of the patient sera recognized multiple SR protein family members in the immunoblots, a likely possibility is that the epitope recognized is common to all of the antigenic proteins. However, a few of the patient sera did show a preference for particular SR protein species. Interestingly, a novel SR protein was recently identified with an ANA positive serum from a patient with hepatocellular carcinoma (Imai et al., 1995).

It already is known that common epitopes are present on SR protein family members from studies with murine monoclonal antibodies (mAbs). One mAb, 104, recognizes a phosphate-dependent epitope in the C-terminal SR domain of all SR protein family members which is characterized by arginine alternating predominantly with phospho-serine (Zahler et al., 1993). Another MAb, 16H3, against the alternating-arginine domain, probably also binds in the SR domain but is not phosphate-dependent (Neugebauer et al., 1995). These observations suggest that common antigenic sites for these proteins reside in the SR domain which is characterized by highly charged stretches of phospho-serine alternating with arginine. Because the SR-reactive patient sera did not react with another alternating-arginine protein, RE-GST, it is unlikely that the autoantibodies which recognize SR proteins do so because of an affinity for either highly charged sequences or alternating-arginine domains in general.

Because the spliceosome contains many proteins with alternating-arginine domains (Neugebauer et al., 1995), the inventor speculates that an initial reactivity to one alternating-arginine protein could lead to the presentation and development of autoimmunity toward other similar domains. It has been suggested that retrovirally encoded gag proteins contain such a charged stretch similar to the alternating arginine domain in the U1 70K protein (Query and Keene, 1987). Perhaps autoreactivity with these additional epitopes present in the alternating-arginine domains of SR proteins is triggered by retroviral infection and the development of immunity towards gag. A distinct mechanism is suggested by the observation that the incidence of Einstein Barr virus (EBV) infection correlates with autoimmune disease in children (James et al., 1997). EBV-infected patients can develop titers to Sm proteins which are prominent components the spliceosome and exist in cells in large complexes with SR proteins (Yitzaki et al., 1996; Kim et al., 1997). However, if this is the case, an additional factor also must be important for the development of autoimmunity, since most of the adult human population has been infected by EBV.

The high prevalence of anti-SR immunoreactivity and high specificity of that reactivity for SLE indicates that the SR protein ELISA test may be as powerful diagnostically as is anti-Sm reactivity in patients with SLE. Of the various diagnostic tests available, the most specific autoimmune antigens (e.g., anti-ribosomal P proteins, anti-PCNA) are only recognized by a small fraction of the patients, while the more highly prevalent markers (e.g., anti-histone, anti-U1 RNP) are less specific for SLE among autoimmune diseases in general (Tan, 1997). Only anti-dsDNA and anti-Sm reactivity are highly specific for SLE, yet these markers do not identify 100% of the patients with SLE. Therefore, the SR protein ELISA test would be a useful test to add to the diagnostic series. Because some data indicates that anti-dsDNA reactivity follows flaring of disease in any given patient quite closely and may be useful in determining therapy (Ting and Hsieh, 1992; Zonana-Nacach et al., 1995; Esdaile et al., 1996), it will be of interest to determine the extent to which anti-SR reactivity varies with flares.

In addition to providing a highly specific test for SLE, reactivity with SR proteins correlates highly with patients having both SLE and APLA. Though initially associated with SLE, APLS has been increasingly recognized as a distinct disorder over the past ten years. It is associated with autoreactivity to phospholipids and recurrent thrombolitic events (Harris, 1989; Alarcon-Segovia and Sanchez-Guerrero, 1989; Asherson et al., 1989; Lockshin, 1994; Khamashta and Hughes, 1995). Of a group of patients with both disorders, the inventor found that 59% react with SR proteins. In contrast, 36% of patients with SLE alone reacted while only 19% of patients with primary APLS reacted. It will be of interest to consider a longitudinal study of APLS patients who become positive for SR proteins and may subsequently develop SLE. A lack of reactivity with SR proteins in APLS patients may indicate that the syndrome may be restricted to APLS and not advance to SLE. These possibilities will be the subject of future studies.

Finally, the inventor showed that post-translational modification of SR proteins provides an important component of the autoreactivity. Dephosphorylation of SR proteins resulted in the pronounced loss or acquisition of antigen recognition (see FIG. 7). Like SR proteins, two other antigens which are excellent markers for SLE, RNA polymerase I (pol I; Picking et al., 1990; Stetler et al., 1992) and the Sm D protein (Rokeach et al., 1992; Ou et al., 1997), contain epitopes generated by post-translational modification. Interestingly, autoreactivity with a phospho-epitope on pol I is observed early in an MRL mouse model for SLE; this is followed by reactivity to both phosphorylated and dephosphorylated pol I epitopes later in the development of autoimmunity (Stetler et al., 1992). Neither pol I nor SmD retains antigenicity when expressed in bacteria, and purification of these native antigens in quantities required for broad diagnostic use is very difficult (Picking et al., 1990; Stetler et al., 1992; Rokeach et al., 1992; Ou et al., 1997). In this regard, the use of SR proteins in a diagnostic test is aided by the ease with which it is possible to purify the post-translationally modified proteins from human cells or animal tissues (Zahler et al., 1992; Zahler et al., 1993). A routine purification of SR proteins from 100 grams of HeLa cells yields protein sufficient for 4000 ELISA test wells (approximately 0.4 mg).

The observation that many of the autoepitopes on SR proteins are phosphate-sensitive has important ramifications for understanding the initiation and development of autoimmunity. Reactivity of patient sera with SR proteins was observed to either disappear upon dephosphorylation or, conversely, dramatically improve, suggesting that the anti-SR antibodies in any given patient serum must bind one or a small number of epitopes. Because multiple members of the SR protein family were recognized by each serum, these dominant epitopes must also be shared among family members. In that these particular autoepitopes may resemble epitopes introduced by foreign agents, such as viruses, further examination of the precise determinants is warranted. In addition, it will be of interest to learn whether patients can be subdivided in meaningful ways with respect to case history and/or therapy based.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Abbondanzo et al., *Breast Cancer Res. Treat.,* 16: 182 (#151), 1990.
Aebersold et al., *Proc. Natl. Acad. Sci.,* 84:6970–6974, 1987.
Alarcon-Segovia and Sanchez-Guerrero, *J. Rheumatol,* 16:482–488, 1989.
Allred et al., *Breast Cancer Res. Treat.,* 16: 182(#149), 1990.
Asherson et al., *Medicine* 68:366–374, 1989.
Baichwal and Sugden, In: *Gene Transfer,* Kucherlapati R., ed., New York, Plenum Press, pp. 117–148, 1986.
Barany and Merrifield, "The Peptides, Gross and Meienhofer, eds", *Academic Press, New York,* 1–284, 1979.
Benvenisty and Reshef, *Proc. Natl. Acad. Sci.,* 83(24):9551–5, 1986.
Birney et al., *Nucleic Acids Res.,* 21:5803–5816, 1993.
Brown et al., *Breast Cancer Res. Treat.,* 16: 192(#191), 1990.
Cáceres and Krainer, *EMBO J.,* 12:4715–4726, 1993.
Cáceres et al., *Science,* 265:1706–1709, 1994.
Capaldi et al., *Biochem. Biophys. Res. Comm.,* 76:425, 1977.
Casals et al., *Arthritis Rheum.,* 7:379–390, 1964.
Chang et al., *Hepatology,* 14:124A, 1991
Chase, M., *Proc. Soc. Exp. Biol. Med.,* 61:257, 1946.
Chen and Okayama, *Mol. Cell Biol.,* 7:2745–2752, 1987.
Coffin, In: Fields B N, Knipe D M, ed. Virology, New York: Raven Press, pp. 1437–1500, 1990.
Cohen et al., *Bull. Rheum. Dis.,* 21:643, 1971.
Colwill et al., *EMBO J.,* 15:265–275, 1996.
Couch et al., *Am. Rev. Resp. Dis.,* 88:394–403, 1963.
Coupar et al., *Gene,* 68:1–10, 1988.
Crowther, "ELISA;Theory and Practice", In *Methods in Molecule Biology* Vol. 42; Publ. Humana Press; New Jersey, 1995.
Dignam et al., *Nucleic Acids Res.,* 11:1475–1489, 1983.
Dubensky et al., *Proc. Nat. Acad. Sci. USA,* 81:7529–7533, 1984.
Edwards et al., *Ann. Rheum. Dis.,* 46:773–6, 1987.
Ellis et al., *Annals of Allergy, Asthma, & Immunology,* 79:151–154, 1997.
Engvall and Perlmann, *Immunochem.* 8:871–873, 1971.
Engvall *Methods Enzymol,* 70 (A) p419–39, 1980.
Engvall, *Lancet,* 2 (8000) p1410, 1976.
Engvall, *Med Biol.,* 55(4) p193–200, 1977.
EP 373908
Esdaile et al., *J. Rheumatol.,* 23:1891–1896, 1996.
Fechheimer et al., *Proc. Natl. Acad. Sci. USA,* 84:8463–8467, 1987.
Ferkol et al., *FASEB J.,* 7:1081–1091, 1993.
Fraley et al., *Proc. Natl. Acad. Sci. USA,* 76:3348–3352, 1979.
Freshner, *Animal Cell Culture: a Practical Approach* Second Edition, Oxford/New York, IRL Press, Oxford University Press, 1992.
Friedmann, *Science,* 244:1275–1281, 1989.
Fu and Maniatis, *Science,* 256:535–538, 1992.
Fu, *Nature,* 365:82–85, 1993.
Fu, *RNA,* 1:663–680, 1995.
Ge and Manley, *Cell,* 62:25–34, 1990.
Genbank sequence HSU30826
Genbank sequence HSU30828
Genbank sequence HUMSC35
Genbank sequence HUMSF2P33
Genbank sequence HUMSRP20
Genbank sequence HUMSRP75
Ghosh-Choudhury et al., *EMBO J.,* 6:1733–1739, 1987.
Ghosh and Bachhawat, *Targeted Diagnosis & Therapy.* 4:87–103, 1991.
Gladman, D. D., *Cut. Opin. Trheum.,* 1992.
Gomez-Foix et al., *J. Biol. Chem.,* 267:25129–25134, 1992.
Gopal, *Mol. Cell Biol.,* 5:1188–1190, 1985.
Graham and Prevec, *Biotechnology,* 20:363–390, 1992.
Graham and Prevec, In: E. J. Murray (ed.), Methods in Molecular Biology: Gene Transfer and Expression Protocol, Clifton, N.J.: Humana Press, 7:109–128, 1991.
Graham and Van Der Eb, *Virology,* 52:456–467, 1973.
Graham et al., *J. Gen. Virol.,* 36:59–72, 1977.
Gripenberg et al., *Scand J Immunol.,* 7 (2) p151–7, 1978.
Grunhaus and Horwitz, *Seminar in Virology,* 3:237–252, 1992.
Gui et al., *Nature,* 369:678–682, 1994.
Hager and Burgess, *Anal. Biochem.,* 109:76–86, 1980.
Harland and Weintraub, *J. Cell Biol.,* 101:1094–1099, 1985.
Harris, *Curr. Op. Rheum.,* 1:215–220, 1989.
Hermonat and Muzycska, *Proc. Nat. Acad. Sci. USA,* 81:6466–6470, 1984.
Hoffman and Grabowski, *Genes Dev.,* 6:2554–2568, 1992.
Horwich et al. *J. Virol.,* 64:642–650, 1990.
Imai et al., *J. Clin. Invest.,* 92:2419–2426, 1995.
James, J. A., et al., *J. Clin. Invest.* 12:3019–3026, 1997.

Johnson et al., In: *Biotechnology And Pharmacy,* Pezzuto et al., eds., Chapman and Hall, New York, 1993.
Jones and Shenk, *Cell,* 13:181–188, 1978.
Kaneda et al., *Science,* 243:375–378, 1989.
Karlsson et al., *EMBO J.,* 5:2377–2385, 1986.
Kato et al., *J. Biol. Chem.,* 266:3361–3364, 1991.
Khamashta and Hughes, *Curr. Op. Rheumatol.,* 7:389–394, 1995.
Kim et al., *Genes Dev.,* 6:2569–2579, 1992.
Kim et al., *J. Cell Biol.,* 136:19–28, 1997.
Kimberly, R. P., *Rheum. Dis. Clin. North Am.,* 14:203–21, 1988.
Klein et al., *Nature,* 327:70–73, 1987.
Kohtz et al., *Nature,* 368:119–124, 1994.
Krainer et al., *Cell,* 66:383–394, 1991.
Kraus and Lis, *Mol. Cell. Biol.,* 14:5360–5370, 1994.
Kuby J., "Antigen-Antibody Interactions" In *Immunology,* Second Ed., Publ. W. H. Freeman and Company; New York, 1994.
Kyte and Doolittle, *J. Mol. Biol.,* 157(1):105–132, 1982.
Lane et al., *J. Prot. Chem,* 10:151–160, 1991.
Lavigueur et al., *Genes Dev.,* 7:2405–2417, 1993.
Levrero et al., *Gene,* 101: 195–202, 1991.
Lieberman, J. D., *Rheum. Dis. Clin. North. Am.,* 14:223–243, 1988.
Lockshin, *Rheum. Dis. Clin. North Am.,* 20:45–58, 1994.
Lubbe et al., *Lancet,* 1361–1363, 1983.
Luo et al., *Endocrinology,* 138:3387–3394, 1997.
Luo et al., *Endocrinology,* 138:4435–4444, 1997.
Macejak and Sarnow, *Nature,* 353:90–94, 1991.
Makler et al., *Transfusion,* 21 (3) p303–12, 1981.
Mann et al., *Cell,* 33:153–159, 1983.
Mermoud et al., *EMBO J.,* 13:5679–5688, 1994.
Merrifield, *Science,* 232: 341–347, 1986.
*Methods in Enzymology,* Guthrie and Fink (eds.), Academic Press, San Diego, Calif., 1991.
*Methods in Enzymology,* Vol. 185, Goeddel (ed.), Academic Press, San Diego, Calif., 1990.
Miller, M. L., *Curr.. Opin. Rheum.,* 4:693–699, 1992.
Mills, J. A., Medical Progress, 33:1871–1879, 1994.
Mohan et al., *J. Exp. Med.,* 1993.
Mulligan, *Science,* 260:926–932, 1993.
Myers, EPO 0273085.
Nakamura et al., In: *Handbook of Experimental Immunology* (4th Ed.), Weir, E., Herzenberg, L. A., Blackwell, C., Herzenberg, L. (eds). Vol. 1, Chapter 27, Blackwell Scientific Publ., Oxford, 1987.
Neugebauer et al., *J. Cell Biol.,* 129:899–908, 1995.
Neugebauer and Roth, *Genes Dev.,* 11 :1148–1159, 1997.
Neugebauer et al., *J. Cell Biol.,* 129:899–908, 1995.
Nicolas and Rubenstein, "In: *Vectors: A survey of molecular cloning vectors and their uses,"* Rodriguez and Denhardt (eds.), Stoneham: Butterworth, pp. 494–513, 1988.
Nicolau and Sene, *Biochim. Biophys. Acta,* 721:185–190, 1982.
Nicolau et al., *Methods Enzymol.,* 149:157–176, 1987.
Ou, Sun, Sharp, Hoch, *Clin. Immunol. Immunopathol.,* 83:310–317, 1997.
Paskind et al., *Virology,* 67:242–248, 1975.
Pelletier and Sonenberg, *Nature,* 334:320–325, 1988.
Peng and Mount, *Mol. Cell Biol.,* 15:6273–6282, 1995.
Perales et al., *Proc. Natl. Acad. Sci.,* 91:4086–4090, 1994.
Petterson et al., *J. Biol. Chem.,* 259:5907–5914, 1984.
Picking et al., *J. Rheumatol,* 17:1308–1313, 1990.
Potter et al., *Proc. Nat'l Acad. Sci. USA,* 81:7161–7165, 1984.
Query and Keene, *Cell,* 51:211–220, 1987.
Reichlin, M., *Rheumatic Disease Clinics of North America,* 20(1):29–43, 1994.
Ridgeway, In: Rodriguez R L, Denhardt D T, ed., Vectors: A survey of molecular cloning vectors and their uses, Stoneham: Butterworth,pp.467–492, 1988.
Ring and Lis, *Mol. Cell Biol.,* 14:7499–7506, 1994.
Rokeach et al., *Gene,* 118 :247–253, 1992.
Rossi et al., *Nature,* 381:80–83, 1996.
Roth et al., *J. Cell Biol.,* 115:587–596, 1991.
Roux et al., *Proc. Nat'l. Acad. Sci. USA,* 86:9079–9083, 1989.
Rupp and Weintgraub, *Cell,* 65:927–937, 1991.
Sambrook et al., *Molecular Cloning: A Laboratory Manual,* Cold Spring Harbor Laboratory Press, Cold Spring Harbor, N.Y., 1989.
Samulski et al., *J. Virol.,* 61:(10):3096–3101, 1987.
Sanger et al., *Proc. Natl. Acad. Sci.,* 74:5463–5467, 1977.
Sarngadharan et al., *Princess Takamatsu Symp,* 15:301–8, 1984.
Scharp et al., *Am. J. Med.,* 52:148, 1972.
Screaton et al., *EMBO J.,* 14:4336–4349, 1995.
Shapiro, S. S., *Annu. Rev. Med.,* 47:533–553, 1996.
Silman et al., *Ann. Rheum. Dis.,* 47:988–92, 1988.
St. Clair et al., *Clin. Immunol. Immunopathol.,* 54:266–280, 1990.
Steinberg and Steinberg, *Arthritis. Rheum.,* 34:945–950, 1991.
Stetler et al., *Autoimmunity,* 12:29–36, 1992.
Stewart and Young, Solid Phase Peptide Synthesis, 2d. ed., Pierce Chemical Co., 1984.
Sun et al., *Genes Dev.,* 7:2598–2608, 1993.
Suzuki et al.,*Ann. de Medecine Interne,* 147:248–252, 1996.
Swaak et al., *Ann. Rheum. Dis.,* 45:359–66; 1986.
Tacke and Manley, *EMBO J.,* 14:3540–3551, 1995.
Tam et al., *J. Am. Chem. Soc.,* 105:6442, 1983
Tan et al., *Arth. Rheum.,* 40:1601–1611, 1997.
Tan et al., *Adv. Immunol.,* 44:93–151, 1989.
Tan, E. M., *Arthritis Rheum,* 25:1271–1277, 1982.
Tan, E. M., *Annals NY Acad. Med.,* 815:1–14, 1997.
Tan et al., *J. Clin. Invest.,* 82:1288–1294, 1966.
Tazi et al., *Nature,* 363:283–286, 1993.
Temin In: *Gene Transfer,* Kucherlapati (ed.), New York: Plenum Press, pp. 149–188, 1986.
ter Borg, E. J. et al., *Arthritis Rheum.,* 33:634–43, 1990.
Teuber et al., *Clin. Rheum.,* 14:667–72, 1995.
Teuber et al., *West. J. Med.,* 162:418–425, 1995.
Tian and Maniatis, *Cell,* 74:105–114, 1993.
Tian and Maniatis, *Genes Dev.,* 8:1703–1712, 1994.
Ting and Hsieh, *Ann. Rheum. Dis.,* 51:45–51, 1992.
Tomer et al., *Int. Arch. Allergy. Immunol.,* 100:293–306, 1993.
Top et al., *J. Infect. Dis.,* 124:155–160, 1971.
Trentham et al., *N. Engl. J. Med.* 1981, 305, 976–982
Tur-Kaspa et al., *Mol. Cell Biol.,* 6:716–718, 1986.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,367,110
U.S. Pat. No. 4,452,901
U.S. Pat. No. 4,554,101.
U.S. Pat. No. 4,668,621
U.S. Pat. No. 5,071,745
U.S. Pat. No. 5,320,940

Utz et al., *J. Exp. Med.,* 187:547–560, 1998.
Valcárcel and Green, *TIBS,* 21:296–301, 1996.
van Vollenhoven et al., *Arthritis & Rheumatism,* 38:1826–1831, 1995.
Varmus et al., *Cell,* 25:23–36, 1981.
Venables, P. J. W., *British Medical Journal,* 307:663–666, 1993.
Vyse and Walport, *Br. F Hosp. Med.,* 50:121–132, 1993.
Wagner et al., *Proc. Natl. Acad. Sci.,* 87(9):3410–3414, 1990.
Wallace et al., *Arthritis Rheum.* 1979, 22, 703–710
Wang and Manley, *RNA,* 1:335–346, 1995.
Wang et al., *RNA,* 1:335–346, 1995.
Wassarman and Steitz, *Proc. Natl. Acad. Sci. USA,* 90:7139–7143, 1993.
Watakabe et al., *Genes Dev.,* 7:407–418, 1993.
Weidermann and Miescher, *Ann. N.Y. Acad. Sci.,* 124:807, 1965.
Weinberg et al., *J. Clin. Invest.,* 92:596–602, 1993.
Weiner, H., *Science,* 259:1321, 1993.
Wilke et al., *Clin. Exp. Rheumatol.,* 9:581–587, 1991.
Wong et al., *Gene,* 10:87–94, 1980.
Woppman et al., *Nucleic Acids Res.,* 21:2815–2822, 1993.
Wu and Maniatis, *Cell,* 75:1061–1070, 1993.
Wu and Wu, *Adv. Drug Delivery Rev.,* 12:159–167, 1993.
Wu and Wu, *Biochemistry,* 27:887–892, 1988.
Wu and Wu, *J. Biol. Chem.,* 262:4429–4432, 1987.
Yang et al., *Proc. Natl. Acad. Sci USA,* 87:9568–9572, 1990.
Yitzaki et al., *Proc. Natl. Acad. Sci.,* 93:8830–8835, 1996.
Zahler and Roth, *Proc. Natl. Acad. Sci. USA,* 92:2642–2646, 1995.
Zahler et al., *Genes Dev.,* 6:837–847, 1992.
Zahler et al., *Science,* 260:219–222, 1993.
Zamore and Green, *EMBO J.,* 10:207–214, 1991.
Zelenin et al., *FEBS Lett.,* 280:94–96, 1991.
Zonana-Nacach et al., *J. Rheumatol.,* 22(1):45–9, 1995.
Zuo and Manley, *EMBO J.,* 12:4727–4737, 1993.
Zuo and Manley, *Proc. Natl. Acad. Sci. USA,* 91:3363–3367, 1994.

What is claimed is:

1. A method of diagnosing an autoimmune disease in a mammal comprising:
   a) obtaining an antibody-containing sample from said mammal;
   b) contacting said sample with a composition comprising an isolated SR antigen; and
   c) detecting the presence of an SR antigen/anti-SR antibody complex;
      wherein the presence of an SR antigen/anti-SR antibody complex is diagnostic for an autoimmune disease.

2. The method of claim 1, wherein said autoimmune disease is a systemic autoimmune disease.

3. The method of claim 2, wherein said systemic autoimmune disease is selected from the group consisting of systemic lupus erythematosus (SLE), mixed connective tissue disease (MCTD), progressive systemic scleroderma (PSS), antiphospholipid syndrome (APLS), and a combination of SLE and APLS.

4. The method of claim 1, wherein said sample is blood, plasma or serum.

5. The method of claim 1, wherein said detecting comprises a technique selected from the group consisting of ELISA, RIA, immunoprecipitation and Western blotting.

6. The method of claim 5, wherein said ELISA is a sandwich ELISA.

7. The method of claim 1, wherein step (b) comprises:
   i) providing a preparation comprising an isolated SR antigen bound to a support;
   ii) contacting said preparation with said sample whereby an SR antigen/anti-SR antibody complex is formed; and
   iii) contacting said complex with a detection agent.

8. The method of claim 7, wherein said agent is an anti-Fc antibody that binds said anti-SR antibody.

9. The method of claim 8, wherein said anti-Fc antibody is labeled with a label selected from the group consisting of a radiolabel, an enzyme, biotin, a dye, a fluorescent tag label, a hapten and a luminescent label.

10. The method of claim 9, wherein said fluorescent tag is selected from the group consisting of fluorescein, rhodamine, luciferase and green fluorescent protein.

SEQUENCE LISTING

<160> NUMBER OF SEQ ID NOS: 1

<210> SEQ ID NO 1
<211> LENGTH: 40
<212> TYPE: PRT
<213> ORGANISM: Artificial Sequence
<220> FEATURE:
<223> OTHER INFORMATION: Description of Artificial Sequence:  SYNTHETIC

<400> SEQUENCE: 1

```
Lys Asp Arg Lys Asp Arg Glu Arg Glu Arg Glu Arg Glu Arg Arg Glu
 1               5                  10                  15

Arg Glu Arg Glu Arg Glu Lys Glu Arg Glu Lys Glu Lys Glu Arg Glu
            20                  25                  30

Arg Asp Arg Glu Arg Asn Ser Glu
        35                  40
```

11. The method of claim 9, wherein said dye is selected from the group consisting of phycoerythrin, phycocyanin, allophycocyanin, texas red and o-phthaldehyde.

12. The method of claim 9, wherein said enzyme is alkaline phosphatase, or horseradish peroxidase.

13. The method of claim 7, wherein said support is a microtitre plate, a polystyrene bead, test tube or dipstick.

14. The method of claim 7, wherein said isolated SR antigen is bound to said support using an anti-SR protein antibody.

15. The method of claim 7, wherein said isolated SR antigen is covalently bound to said support.

16. The method of claim 1, wherein said isolated SR antigen comprises SR-antigen bound by a labeled anti-SR antibody and said detecting comprises measuring a decrease in the intensity of the bound label signal, caused by antibodies in the said sample competitively displacing the labeled anti-SR antibody.

* * * * *